United States Patent
Chung et al.

(10) Patent No.: US 10,405,732 B2
(45) Date of Patent: Sep. 10, 2019

(54) ENDOSCOPE DEVICE INCLUDING A KNOB DRIVER

(71) Applicant: SAMSUNG ELECTRONICS CO., LTD., Suwon-si (KR)

(72) Inventors: Hae-In Chung, Anyang-si (KR); Mun-Kue Park, Suwon-si (KR); Yong-Hee Lee, Seoul (KR); Jin-Won Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1373 days.

(21) Appl. No.: 14/486,475

(22) Filed: Sep. 15, 2014

(65) Prior Publication Data
US 2015/0080658 A1 Mar. 19, 2015

(30) Foreign Application Priority Data

Sep. 13, 2013 (KR) .................. 10-2013-0110323

(51) Int. Cl.
*A61B 1/00* (2006.01)
*A61B 1/005* (2006.01)

(52) U.S. Cl.
CPC ........ *A61B 1/00006* (2013.01); *A61B 1/0016* (2013.01); *A61B 1/0052* (2013.01); *A61B 1/0057* (2013.01)

(58) Field of Classification Search
CPC . A61B 1/00006; A61B 1/0016; A61B 1/0052; A61B 1/0057
See application file for complete search history.

(56) References Cited

U.S. PATENT DOCUMENTS

| | | | |
|---|---|---|---|
| 4,469,091 A | 9/1984 | Slanetz, Jr. | |
| 4,499,895 A | 2/1985 | Takayama | |
| 4,503,842 A | 3/1985 | Takayama | |
| 4,559,928 A | 12/1985 | Takayama | |
| 5,575,755 A * | 11/1996 | Krauter | A61B 1/0052 600/148 |
| 5,626,553 A * | 5/1997 | Frassica | A61B 1/0052 600/146 |
| 6,210,337 B1 * | 4/2001 | Dunham | A61B 1/0052 600/462 |
| 6,932,761 B2 * | 8/2005 | Maeda | A61B 1/0016 600/104 |
| 2004/0059191 A1 * | 3/2004 | Krupa | A61B 1/0052 600/146 |
| 2005/0272975 A1 * | 12/2005 | McWeeney | A61B 1/00071 600/113 |

(Continued)

*Primary Examiner* — Timothy J Neal
*Assistant Examiner* — Jae Woo
(74) *Attorney, Agent, or Firm* — Sughrue Mion, PLLC

(57) ABSTRACT

Provided is an endoscope device and a method of operating the endoscope device. The endoscope device includes: a knob driving part configured to be driven in a mode selected by an operator from either of an automatic mode and a manual mode; a bending part connected to the knob driving part and configured to change a position of a distal end of the endoscope device by driving of the knob driving part, a power generating part configured to provide power to the knob driving part; and a power transmitting part configured to drive the power generating part according to a manipulation of the knob driving part.

30 Claims, 15 Drawing Sheets

(56) References Cited

U.S. PATENT DOCUMENTS

| Publication No. | Date | Inventor | Classification | Subclass |
|---|---|---|---|---|
| 2006/0252993 A1* | 11/2006 | Freed | A61B 1/0052 | 600/146 |
| 2007/0232857 A1* | 10/2007 | Otawara | A61B 1/00098 | 600/129 |
| 2008/0033284 A1* | 2/2008 | Hauck | A61B 1/0052 | 600/424 |
| 2008/0188868 A1* | 8/2008 | Weitzner | A61B 1/0014 | 606/130 |
| 2009/0012365 A1* | 1/2009 | Ueno | A61B 1/0052 | 600/146 |
| 2009/0287188 A1* | 11/2009 | Golden | A61M 25/0147 | 604/528 |
| 2010/0217072 A1* | 8/2010 | Kondoh | A61B 1/00071 | 600/101 |
| 2011/0288375 A1* | 11/2011 | Ouchi | A61B 1/0052 | 600/114 |
| 2012/0046522 A1* | 2/2012 | Naito | A61B 1/00006 | 600/118 |
| 2012/0220832 A1* | 8/2012 | Nakade | A61B 1/0052 | 600/149 |
| 2013/0102961 A1* | 4/2013 | Konstorum | A61B 1/00066 | 604/95.04 |
| 2013/0205937 A1* | 8/2013 | Arai | A61B 1/0052 | 74/527 |
| 2013/0310650 A1* | 11/2013 | Hales | A61B 1/267 | 600/188 |
| 2014/0180008 A1* | 6/2014 | Okamoto | A61B 1/00002 | 600/132 |
| 2014/0246014 A1* | 9/2014 | Petersen | A61B 1/0052 | 128/200.26 |
| 2014/0309625 A1* | 10/2014 | Okamoto | A61B 1/0057 | 606/1 |
| 2014/0316202 A1* | 10/2014 | Carroux | A61B 1/0008 | 600/146 |
| 2014/0371534 A1* | 12/2014 | Okamoto | A61B 1/00066 | 600/118 |
| 2015/0335862 A1* | 11/2015 | Selkee | A61B 1/0052 | 604/95.04 |
| 2016/0030120 A1* | 2/2016 | Yanagihara | A61B 1/0055 | 606/130 |
| 2016/0038718 A1* | 2/2016 | Caples | A61B 18/1492 | 604/95.04 |

\* cited by examiner

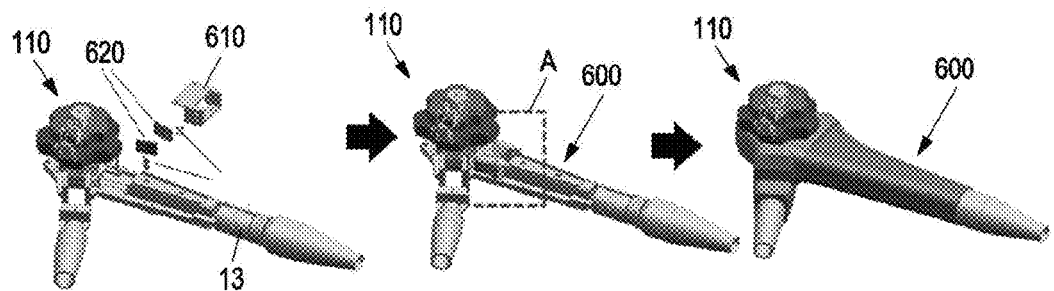
FIG.6A  FIG.6B  FIG.6C
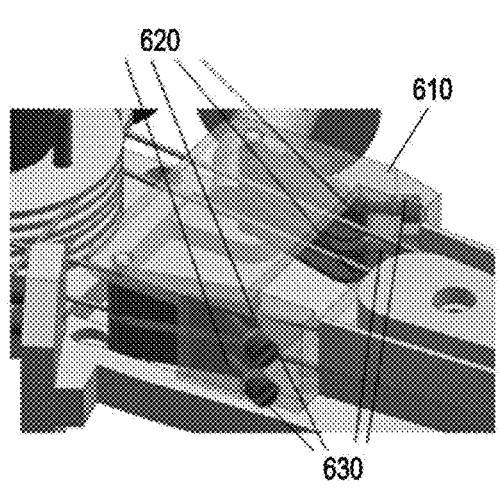 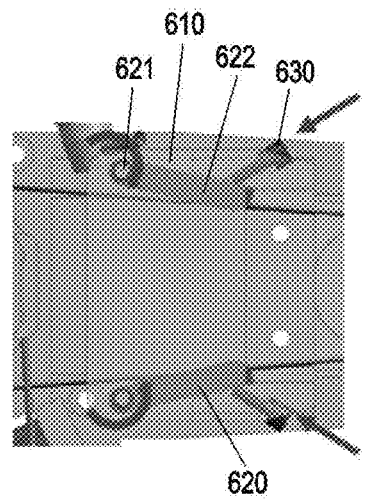
FIG.7A  FIG.7B

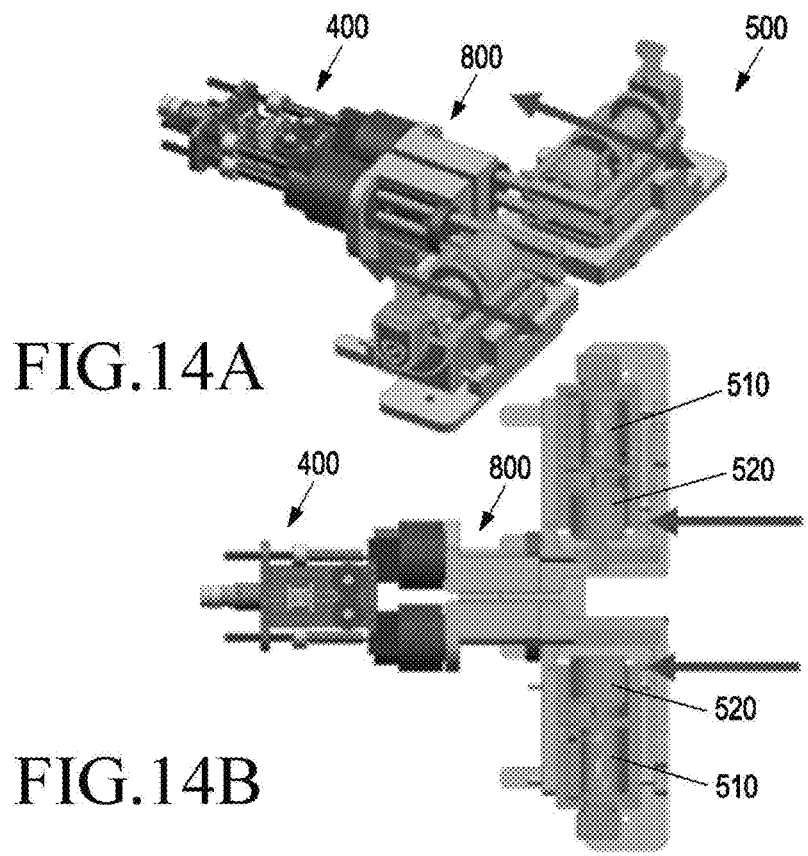
FIG.14A
FIG.14B
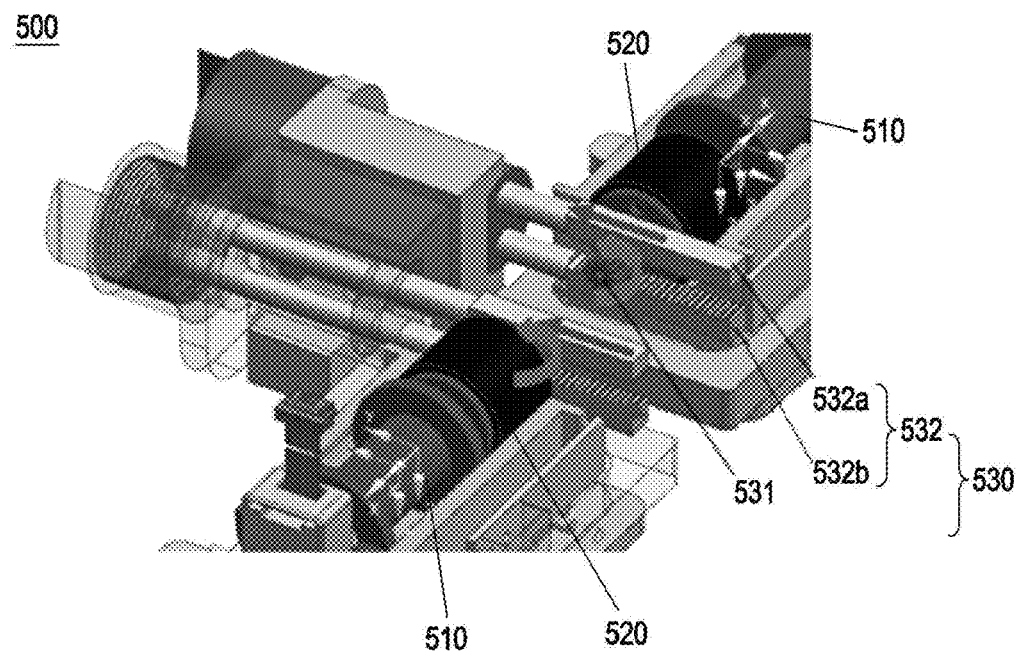
FIG.15

ENDOSCOPE DEVICE INCLUDING A KNOB DRIVER

CROSS-REFERENCE TO RELATED APPLICATION

This application claims priority from Korean Patent Application No. 10-2013-0110323 filed on Sep. 13, 2013 in the Korean Intellectual Property Office, the entire disclosure of which is hereby incorporated by reference.

BACKGROUND

1. Field

Apparatuses and methods consistent with exemplary embodiments relate to an endoscope device.

2. Description of the Related Art

Generally, an endoscope refers to a device that is inserted into the interior of an organ or cavity, for example, the stomach, the large intestine, the S-shape colon, the bronchial organ, or the like, to allow a user to directly see the interior and make a diagnosis. With the increasing interest in health, the endoscope is frequently used in medical check-ups. The endoscope is inserted for a diagnosis into the interior of the body of a subject through the mouth or anus of the subject or an incision of a body part of the subject.

According to a driving method, the endoscope device may be classified as a manually driven endoscope device or an automatically driven endoscope device. The endoscope device that is driven manually largely depends on experience or manipulation skills of an operator. The automatically driven endoscope device does not depend as much on the operator's experience or manipulation skills and may be easily driven, as compared to the manually driven endoscope device. However, for the automatically driven endoscope device, in case of an emergency where a problem occurs in the endoscope device or an examination process during the checkup of the subject, the endoscope device cannot be switched to the manual mode and cannot deal with the emergency during the checkup.

The above information is presented as background information only to assist with an understanding of the present disclosure. No determination has been made, and no admission is made, as to whether any of the above might be applicable as prior art with regard to the present disclosure.

SUMMARY

Aspects of one or more exemplary embodiments address at least the above-mentioned problems and/or disadvantages and to provide at least the advantages described below.

Aspects of one or more exemplary embodiments provide an endoscope device including a knob driving part that enables an operator to manipulate the endoscope device with a small force.

Aspects of one or more exemplary embodiments provide an endoscope device that may be driven in an automatic mode or a manual mode depending on selection, that is, the endoscope device having a knob driving part, such that in a normal situation where an examinee is examined, an operator may easily manipulate the endoscope device with a small force in the automatic mode, and upon occurrence of an emergency situation during the use of the endoscope device in the automatic mode, the automatic mode may be switched to the manual mode.

Aspects of one or more exemplary embodiments provide an endoscope device capable of improving response characteristics when being used in an automatic mode.

Aspects of one or more exemplary embodiments provide an endoscope device capable of sensing a triggering force generated in a front end part of a distal end and providing feedback to an operator.

Aspects of one or more exemplary embodiments provide an endoscope device capable of improving position control precision and minimizing a gap generated during direction change when the operator is examined.

Aspects of one or more exemplary embodiments provide an endoscope device capable of accurately detecting a triggering force corresponding to a driving actuating signal applied to a knob driving part.

Aspects of one or more exemplary embodiments provide an endoscope device capable of facilitating detachment/attachment and coupling of modules provided therein to make sterilization easy and to facilitate replacement of damaged or broken modules, and capable of reducing a gap that may be generated during coupling of the modules or driving of the endoscope device.

Furthermore, aspects of one or more exemplary embodiments provide an endoscope device capable of performing position holding without applying separate locking to a knob driving part.

In addition, aspects of one or more exemplary embodiments provide an endoscope device capable of providing to an operator, feedback, such as haptic feedback, with respect to a factor measured as disturbance after detecting driving torque of a knob driving part.

Other objects to be provided in the present disclosure may be understood from exemplary embodiments described below.

According to an aspect of an exemplary embodiment, there is provided an endoscope device including: a knob driving part configured to be driven in a mode selected by an operator from either of an automatic mode and a manual mode; a bending part connected to the knob driving part and configured to change a position of a distal end of the endoscope device by driving of the knob driving part; a power generating part configured to provide power to the knob driving part; and a power transmitting part configured to drive the power generating part according to a manipulation of the knob driving part.

The knob driving part may include: a knob part configured to receive a triggering force from an operator; and an actuating signal detecting part configured to detect the received triggering force.

The actuating signal detecting part may include: a rotating member in the knob part and configured to transmit a rotation of the knob part to the power generating part and the bending part; a transmitting member on a main shaft of the knob part and configured to transmit the received triggering force applied to the knob part to the rotating member; and a sensor member configured to detect an actuating signal according to the received triggering force.

The rotating member may include: a two-step pulley member in an end part of the transmitting member; a first transmitting wire extending between the two-step pulley member and the power generating part and configured to transmit rotational driving of the two-step pulley member; and a second transmitting wire extending between the two-step pulley member and the bending part and configured to transmit rotational driving of the two-step pulley member.

The two-step pulley member may include: a first two-step pulley part around which the first power transmission wire is wound; and a second two-step pulley part on an upper side or a lower side of the first two-step pulley part and around which the second power transmission wire is wound.

The endoscope device may further include including a first gap reducing device in the knob driving part, the first gap reducing device configured to compensate for a gap of the second power transmission wire between the bending part and the knob driving part.

The first gap reducing device may include: a gap housing provided inside a body of the knob part; a wire contact part rotatably mounted in the gap housing and configured to rotate around a rotation axis to apply a force to the second power transmission wire; and a rotation angle adjusting part configured to adjust a rotation angle of the wire contact part.

The actuating signal detecting part may further include: a pulley coupling part in a lower part of the transmitting member, the pulley coupling part configured to rotatably couple the two-step pulley member; and a sensor coupling part in an upper part of the transmitting member, the sensor coupling part configured to fixedly support the sensor member.

The sensor member may include: a support plate in an upper part of the transmitting member; and a sensor part on the support plate, the sensor part configured to sense rotation of the knob part.

The support plate may include: a through-hole inserted and fixed in the transmitting member; and support protrusions provided to face each other on opposing sides of the through-hole.

The sensor part may include: a pivot module inserted into an another-end terminal of the transmitting member and including an extending arm part; a sensor contact module inserted into the arm part and positioned between the support protrusions; and sensor modules on facing surfaces of the support protrusions and configured to sense a contact by the sensor contact module.

The power generating part may include: one or more driving members configured to provide a driving force; a torque sensor member connected to the one or more driving members; and a gear member connected to the one or more driving members.

The gear member may include: a pinion gear connected to the one or more driving members; and rack gears respectively engaged on a top surface and a bottom surface of the pinion gear.

The power generating part may further include a gap absorbing member configured to control a gap of the power generating part, generated by driving of the one or more driving members.

The gap absorbing member may include: a housing including a seating part on which the power generating part is seated; a gap guide part on the seating part and configured to provide a degree of freedom of translational motion along the rack gears of the power generating part; and a gap elastic part configured to provide elasticity to the power generating part that allows a translational motion to an end part of the seating part on the gap guide part.

The power transmitting part may include: a frame between the knob driving part and the power generating part; a direction change pulley part on the frame and configured to change a direction of the first power transmission wire; a displacement adjusting part movably coupled to the frame and configured to fix the first power transmission wire and to provide a translational motion; and a displacement adjusting elastic part on the displacement adjusting part and configured to provide an elastic force to the displacement adjusting part.

The displacement adjusting part may include: a guide part movably coupled to the frame; and an adjusting guide part coupled to the guide part and configured to fix an end part of the first power transmission wire and to control a degree of freedom in the translational motion of the first power transmission wire.

A coupling device may be between the power transmitting part and the power generating part.

The coupling device may include: a first coupling part on the power transmitting part; and a second coupling part engaged with the first coupling part and on the power generating part, wherein a distance between the power transmitting part and the power generating part is adjusted according to a distance that the first coupling part and the second coupling part are engaged.

The endoscope device may further include: protruding parts extending from the rack gears to the second coupling part, wherein the adjusting guide extends to the first coupling part, such that if the first coupling part and the second coupling part are engaged and coupled to each other, the guide part and the protruding parts contact such that driving of the protruding parts is transmitted to the guide part.

In the automatic mode, a signal corresponding to the received triggering force applied to the knob part may be detected by the actuating signal detecting part and the power generating part may be driven, via the power transmitting part, according to the detected signal.

In the manual mode, the received triggering force applied to the knob part may be provided to the bending part and the power generating part at a same time, to change the position of the distal end.

In the automatic mode: the received triggering force may be detected by the actuating signal detecting part; a driving force may be provided by the power generating part according to the detected triggering force; the driving force of the power generating part may be transmitted to a two-step pulley member of the knob driving part through the power transmitting part; and the driving force transmitted to the two-step pulley member may be transmitted to the bending part to change the position of the distal end.

The power generating part may include a torque sensor member; and in the automatic mode, the torque sensor member may be configured to sense a disturbance and to adjust a rotation speed of the knob part based on a comparison between the sensed disturbance and the detected triggering force.

According to an aspect of another exemplary embodiment, there is provided an endoscope device including: a knob driving part configured to be driven in a mode selected by an operator from either of an automatic mode and a manual mode; a bending part connected to the knob driving part and configured to change a position of a distal end of the endoscope device by driving of the knob driving part; and a power generator configured to provide power to the knob driving part according to a manipulation of the knob driving part, wherein in the automatic mode, a triggering force applied to the knob driving part by an operator of the endoscope device is detected by the knob driving part, and the power generating part is driven to provide a driving force for the knob driving part according to the detected triggering force to change the position of the distal end, and wherein in the manual mode, the detected triggering force applied to the knob driving part is provided to the bending part to change the position of the distal end.

In the automatic mode, the driving force of the power generating part may be transmitted to a two-step pulley member extending between the knob driving part and the power generating part; and the driving force transmitted to the two-step pulley member may be transmitted to the bending part to change the position of the distal end.

The power generating part may include a torque sensor member; and in the automatic mode, the torque sensor member may be configured to sense a disturbance and to adjust a rotation speed of the knob driving part based on a comparison between the sensed disturbance and the detected triggering force.

According to an aspect of another exemplary embodiment, there is provided a method of operating an endoscope device, the method including: detecting a triggering force applied by an operator of the endo scope device to a knob driving part of the endoscope device configured to be driven in a mode selected by an operator from either of an automatic mode and a manual mode; driving, in the automatic mode, a power generating part of the endoscope device according to the detected triggering force, to provide a driving force for the knob driving part according to the detected triggering force so as to change a position of a distal end of the endoscope device; and providing, in the manual mode, the detected triggering force to a bending part of the endoscope device to change the position of the distal end.

The driving the power generating part in the automatic mode may include: transmitting the driving force of the power generating part to a two-step pulley member extending between the knob driving part and the power generating part; and transmitting the driving force transmitted to the two-step pulley member to the bending part to change the position of the distal end.

The driving the power generating part in the automatic mode may include: sensing, by a torque sensor member of the power generating part, a disturbance; and adjusting a rotation speed of the knob driving part based on a comparison between the sensed disturbance and the detected triggering force.

Other aspects, advantages, and salient features of the disclosure will become apparent to those skilled in the art from the following detailed description, which, taken in conjunction with the annexed drawings, discloses various exemplary embodiments.

BRIEF DESCRIPTION OF THE DRAWINGS

The above and other aspects, features and advantages of one or more exemplary embodiments will be more apparent from the following description taken in conjunction with the accompanying drawings, in which:

FIGS. 6A to 6C illustrate a first gap reducing device in an endoscope device according to an exemplary embodiment;

FIGS. 7A and 7B are enlarged views of FIG. 6B;

FIGS. 13A, 13B, 14A, and 14B illustrate a coupled state of a power generating part according to an exemplary embodiment;

FIG. 15 is an enlarged view illustrating a coupled state of a power generating part according to an exemplary embodiment;

DETAILED DESCRIPTION OF EXEMPLARY EMBODIMENTS

Figure 1:
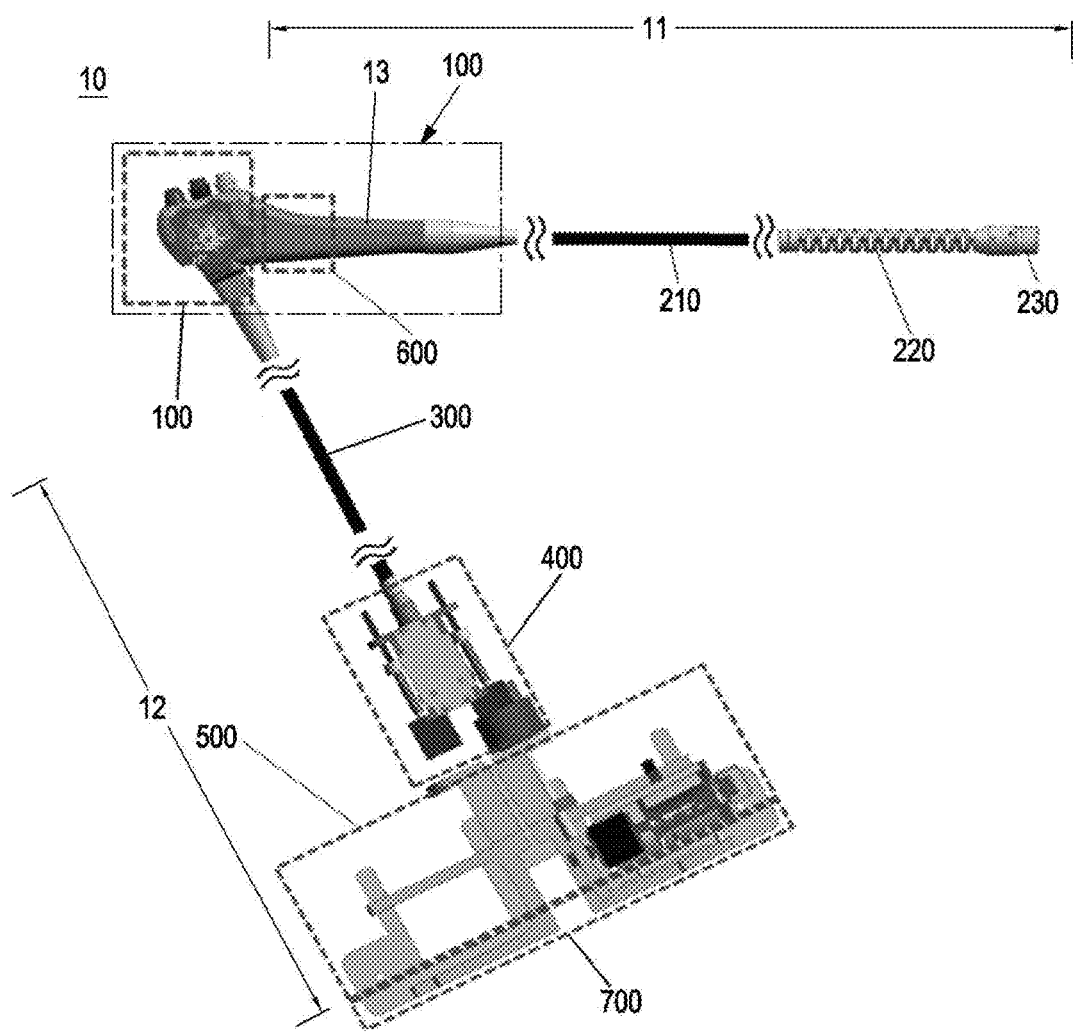
FIG. 1 illustrates an endoscope device according to an exemplary embodiment.

The following description with reference to the accompanying drawings is provided to assist in a comprehensive understanding of various exemplary embodiments as defined by the claims and their equivalents. It includes various specific details to assist in that understanding but these are to be regarded as merely exemplary. Accordingly, those of ordinary skill in the art will recognize that various changes and modifications of exemplary embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of exemplary embodiments is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

For the terms used in various exemplary embodiments of the present disclosure, currently widely used general terms have been selected considering functions in various exemplary embodiments of the present disclosure, but such terms may change according to intentions of those of ordinary skill in the art or cases, or emergence of new technologies. In special cases, there may be terms that are selected arbitrarily by the applicant, and in these cases, meanings of such terms will be explained in detail in the detailed description of exemplary embodiments of the present disclosure. Therefore, the terms used in the exemplary embodiments of the present disclosure may be defined based on the meanings of the terms and the overall contents of the exemplary embodiments of the present disclosure, rather than simply based on names of the terms.

When a part "includes" a component in exemplary embodiments of the present disclosure, it means that the component may further include another component rather than excluding another component, unless the context clearly dictates otherwise. The terms "unit", "module", or the like used in various embodiments of the present disclosure mean a unit for processing at least one function or operation, and may be implemented by hardware, software, or a combination thereof.

Hereinafter, exemplary embodiments will be described in detail with reference to details in the accompanying drawings. However, an exemplary embodiment may not be limited by these exemplary embodiments. Throughout the drawings, identical reference numerals refer to members that perform substantially identical functions.

Hereinafter, an endoscope device 10 according to one or more exemplary embodiments will be described with reference to the accompanying drawings. In the following description, a detailed description of known functions and configurations incorporated herein will be omitted when it may obscure the subject matter of the present disclosure. Terms used herein are defined based on functions in the present disclosure and may vary according to users, operators' intention or usual practices. Therefore, the definition of the terms should be made based on contents throughout the specification.

FIG. 1 illustrates an endoscope device 10 (e.g., endoscope) according to an exemplary embodiment. Referring to FIG. 1, the endoscope device 10 may include a knob driving part 100 (e.g., knob driver), a first member 11 including an insertion tube 210, a bending part 220 (e.g., bending portion), and a distal end 230 in a direction (e.g., first direction) of the knob driving part 100, and a second member 12 including a universal tube 300 and a power generating part 500 in another direction (e.g., second direction) of the knob driving part 100.

Figure 13A:
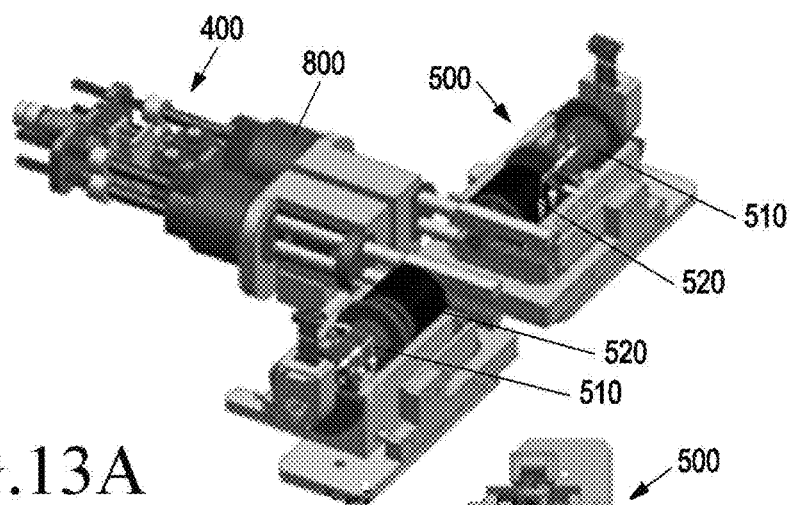
Figure 13B:
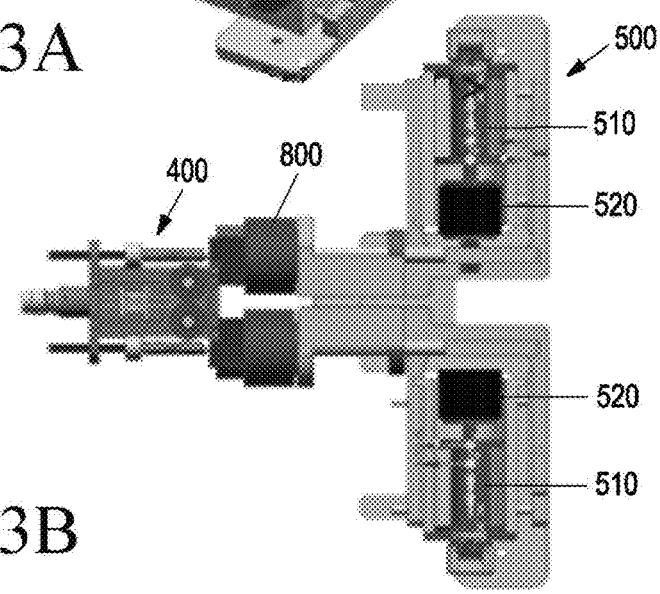

The first member 11 may further include a first gap reducing device 600 (e.g., first gap reducer), and the second member 12 may further include a power transmitting part 400 (e.g., power transmitter) and a gap absorbing device 700 (hereinafter, referred to as a 'third gap reducing device 700') (also refer to FIGS. 13A and 13B).

Figure 2A:
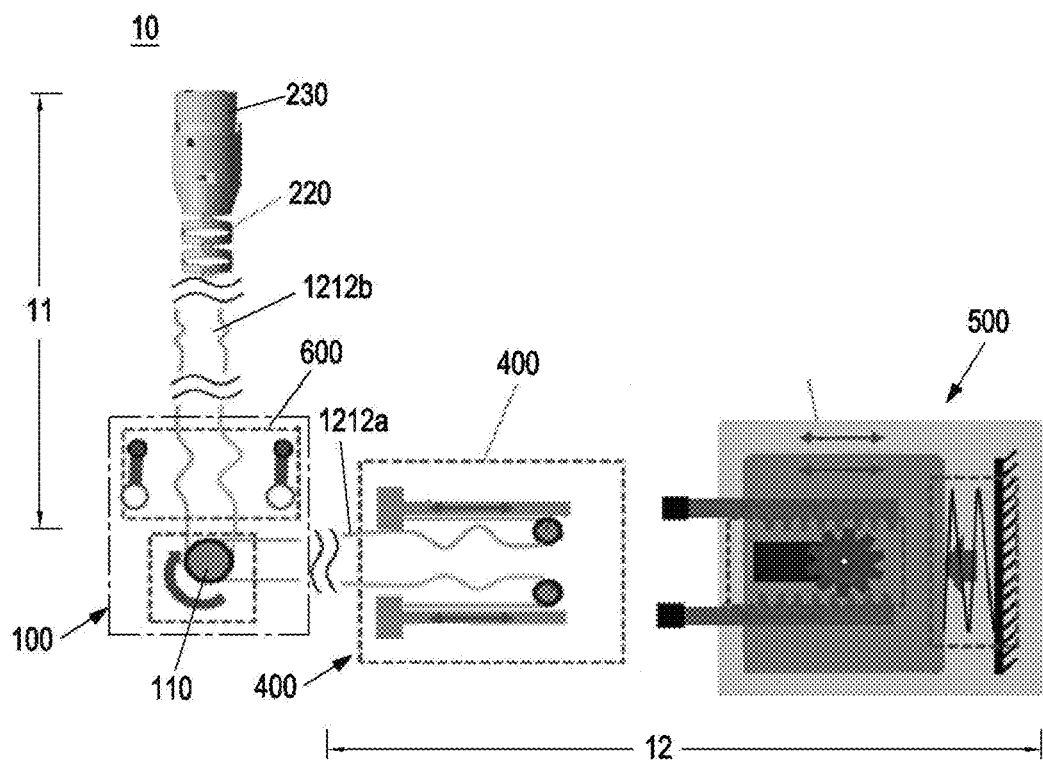
FIG. 2A schematically illustrates an endoscope device according to an exemplary embodiment, in which a power transmitting part and a power generating part are not coupled.
Figure 2B:
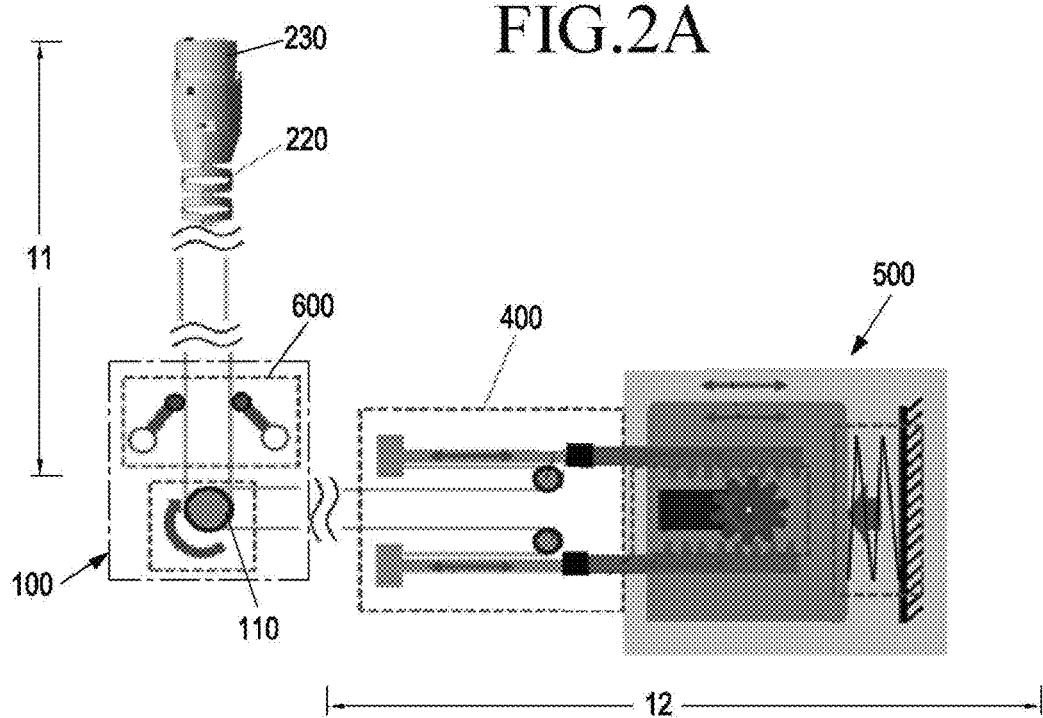
FIG. 2B schematically illustrates an endoscope device according to an exemplary embodiment, in which a power transmitting part and a power generating part have been coupled.

FIGS. 2A and 2B schematically illustrate the endoscope device 10 according to an exemplary embodiment, in which FIG. 2A schematically illustrates the endoscope device 10 before the power transmitting part 400 and the power generating part 500 are coupled and FIG. 2B schematically illustrates the endoscope device 10 after the power transmitting part 400 and the power generating part 500 are coupled. Referring to FIGS. 2A and 2B, the bending part 220 is connected to the knob driving part 100 through a transmission wire (1212, also refer to FIGS. 3A to 3C), more specifically, a second power transmission wire 1212b to be described below, and the power generating part 500 is connected to the knob driving part 100 through the transmission wire 1212, more specifically, a first power transmission wire 1212a to be described below. That is, the knob driving part 100 is simultaneously connected to the bending part 220 and the power generating part 500 for driving for automatic manipulation or driving for manual manipulation.

When the endoscope device 10 according to an exemplary embodiment is driven in an automatic manipulation mode, if the operator operates (e.g., rotates) a knob part 110 (e.g., knob), a triggering force applied by an operator to the knob part 110 is sensed by an actuating signal detection part 120 (e.g., actuating signal detector) (refer also to FIGS. 3C and 4C) for signal detection. A system of the endoscope device 10 drives the power generating part 500 at an operation speed corresponding to a detection signal detected by the actuating signal detection part 120. Thus, the power generating part 500 is driven at the operation speed corresponding to the detection signal. A driving force generated by the power generating part 500 is transmitted (e.g., provided) to a two-step pulley member 1211 (e.g., two-step pulley) (refer also to FIGS. 3A to 3C) through the power transmitting part 400, and the driving force transmitted to the two-step pulley member 1211 changes a position of a front end part 230 (i.e., distal end) through the bending part 220. The endoscope device 10 according to the present exemplary embodiment allows the operator to manipulate the knob part 110 merely with a small amount of force. The endoscope 10 also senses in real time a triggering force applied to the knob part 110 to determine an operation of the endoscope device 10 or to adjust a driving speed of the endoscope 10 (the automatic manipulation mode, refer to FIG. 21). In this regard, the endoscope device 10 or a device connected thereto may include at least one of a processor, a memory, connecting interfaces, etc., to perform storing, detecting, and control operations.

Figure 11:
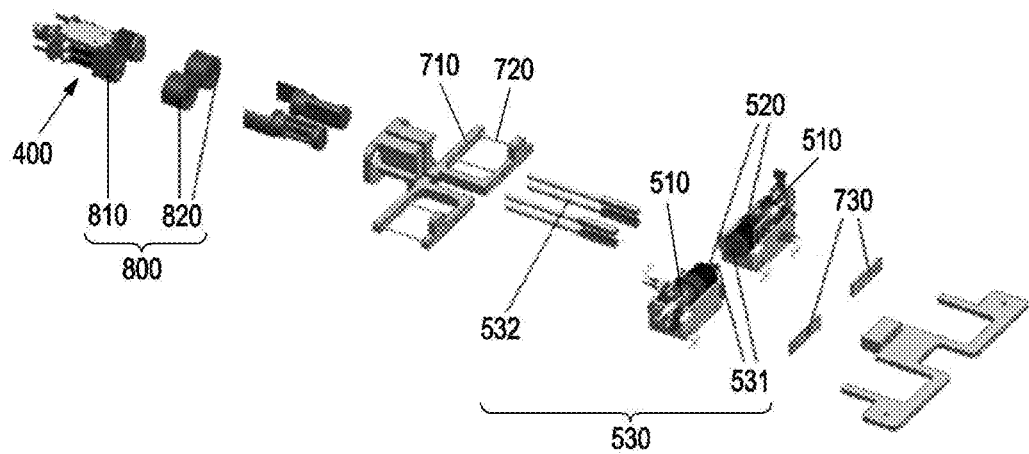
FIG. 11 illustrates a power transmitting part according to an exemplary embodiment.

The power generating part 500 may further include a driving member 510 (e.g., driver) and a torque sensor member 520 (e.g., torque sensor) connected thereto (refer to FIG. 11). The system of the endoscope device 10 stores a sensing signal of the torque sensor member 520 corresponding to normal driving and detects a real-time sensing signal sensed in real time by the torque sensor member 520. The system of the endoscope device 10 compares the real-time sensing signal of the torque sensor member 520 with the sensing signal corresponding to normal driving to determine whether to provide haptic feedback. That is, the torque sensor member 520 senses a change in a triggering force, for example, a change in a triggering force, caused by a source or disturbance other than the triggering force applied to the knob part 110. The system of the endoscope device 10 adjusts driving of the driving member 510 through a sensing signal of the torque sensor member 520 and provides feedback to a user, thus informing the user of an external factor that changes the driving force (a haptic feedback providing mode, see FIG. 22).

On the other hand, when the endoscope device 10 according to an exemplary embodiment is driven in a manual manipulation mode, if the operator rotates the knob part 110, the triggering force applied by the operator to the knob part 110 is provided to the bending part 220 and the power generating part 500 at the same time. As the bending part 220 and the power generating part 500 are simultaneously driven in the manual manipulation mode, the position of the front end part 230 is changed (the manual manipulation mode).

The endoscope device 10 having the above-described operation and structure will be described in more detail.

Figures 3A, 3B:
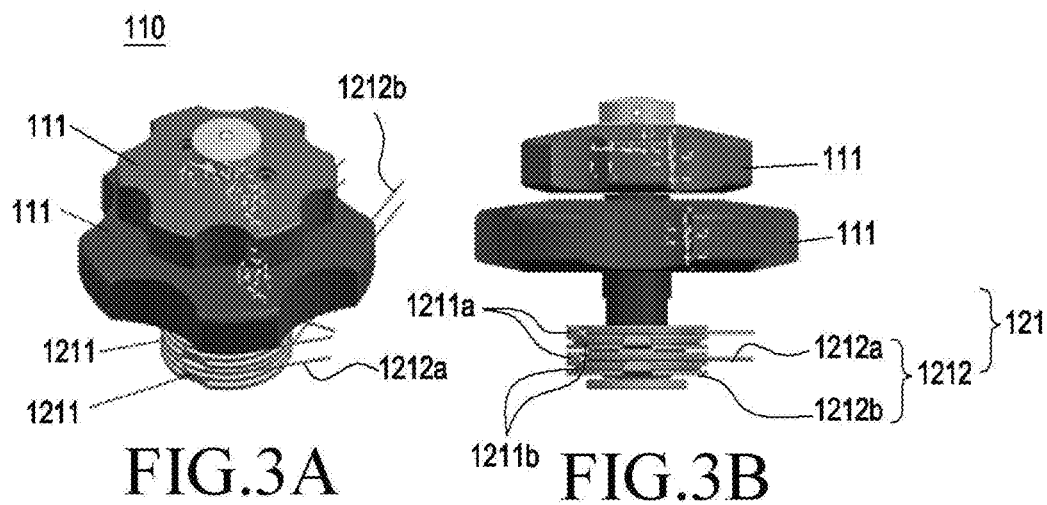
FIGS. 3A to 3C illustrate a knob driving portion according to an exemplary embodiment from various angles.
Figure 3C:
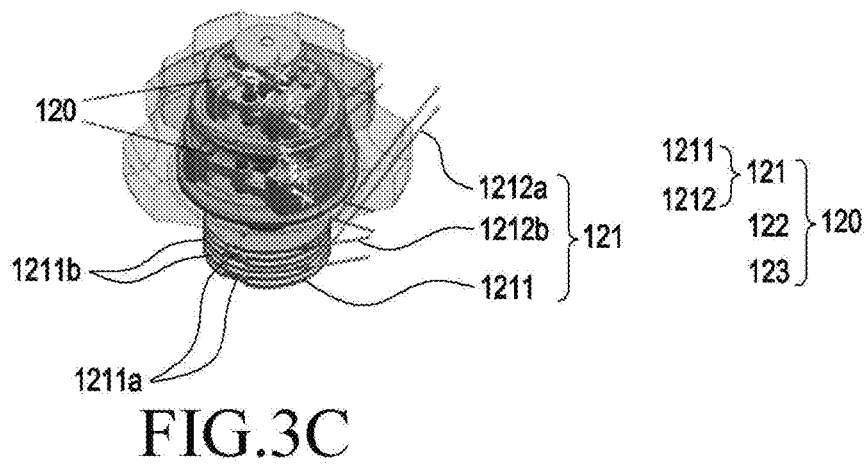
Figure 4A:
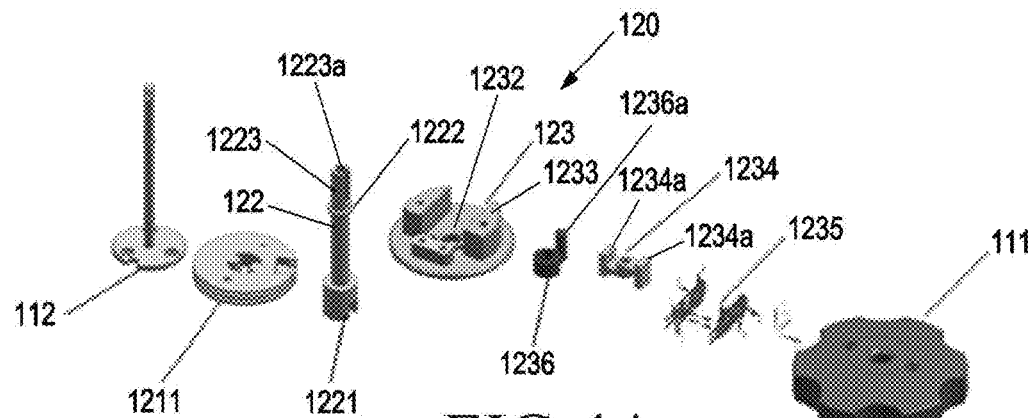
FIGS. 4A to 4C illustrate a state where a knob driving part is exploded or coupled according to an exemplary embodiment.
Figure 4B:
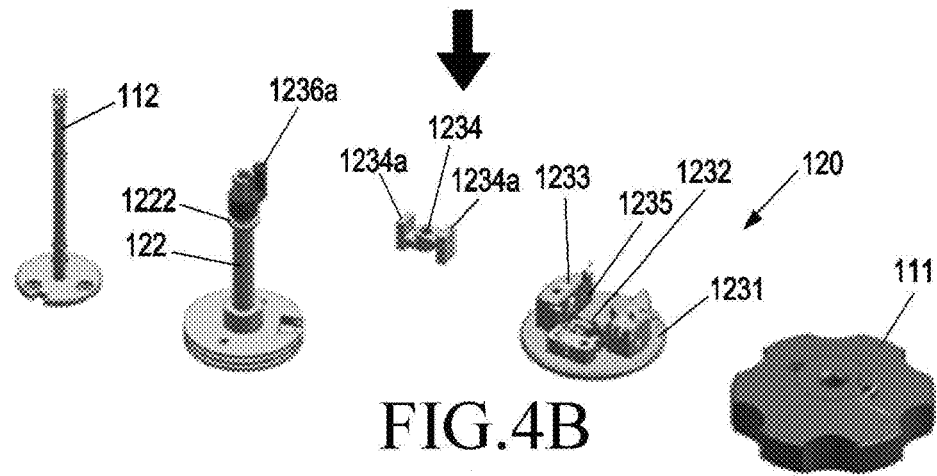
Figure 4C:
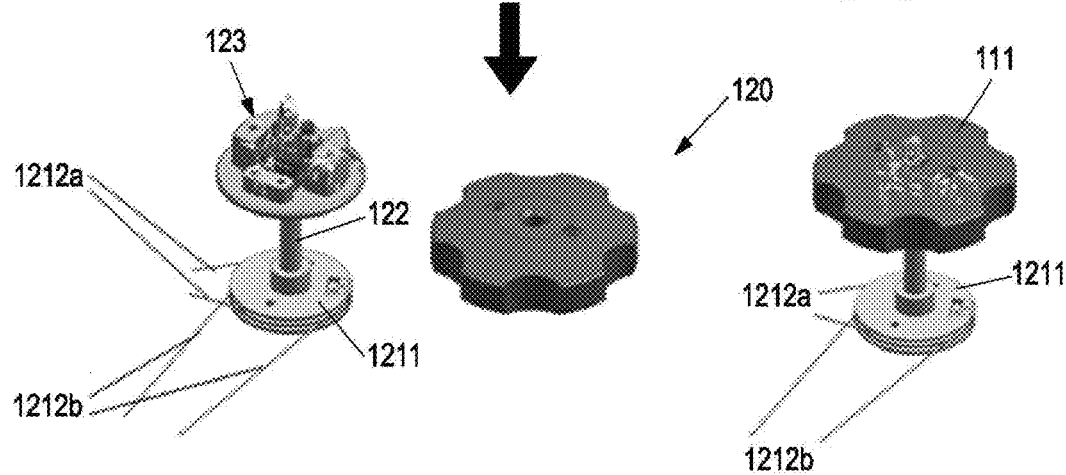

FIGS. 3A to 3C illustrate the knob driving part 100 according to an exemplary embodiment from various angles, and FIGS. 4A to 4C illustrate a state or view where the knob driving part 100 is exploded (i.e., decoupled) or coupled according to an exemplary embodiment.

Referring to FIGS. 3A to 3C and 4A to 4C, the knob driving part 100 according to an exemplary embodiment may include the knob part 110, the actuating signal detection part 120, and the first gap reducing device 600. The knob part 110 is structured to receive a triggering force for manipulation, and may include a knob 111 and a main shaft 112, such that the operator can manipulate driving of the first member 11 through the knob 111.

A plurality of knob parts 110 may be provided, for example, along a driving direction of the front end part 230, and in an exemplary embodiment, a pair of knob parts 110 may be provided to drive the front end part 230 in a first direction (for example, a left or right direction) and in a second direction that is different from the first direction (for example, the first direction may be an upward direction and the second direction may be a downward direction). Each of the actuating signal detection part 120 and the two-step pulley member 1211 may also be provided in pairs for driving in the first direction and in the second direction.

The actuating signal detection part 120 detects an actuating signal of the knob part 110 based on a triggering force applied to the knob part 110. The actuating signal detection part 120 may include a rotating member 121 (e.g., rotator), a transmitting member 122 (e.g., transmitter), and a sensor member 123 (e.g., sensor).

The rotating member 121 is provided in the knob part 110 to transmit (e.g., provide) rotation of the knob part 110 to the power generating part 500 and the bending part 220. The rotating member 121 may include the transmission wire 1212 and the two-step pulley member 1211.

The transmission wire 1212 connects the power generating part 500 to the two-step pulley member 1211 and connects the bending part 220 to the two-step pulley member 1211 to transmit rotational driving of the two-step pulley member 1211. The transmission wire 1212 may include a first power transmission wire 1212a and a second power transmission wire 1212b. The first power transmission wire 1212a is wound or provided between the rotating member 121, more specifically, a first two-step pulley part 1211a (e.g., first two-step pulley), and the power transmitting part 400 to connect the rotating member 121 with the power generating part 500 via the power transmitting part 400. The second power transmission wire 1212b is wound or provided between the rotating member 121, more specifically, a second two-step pulley part 1211b (e.g., second two-step pulley), and the bending part 220 to connect the rotating member 121 with the bending part 220. Thus, the power transmitting part 400 and the bending part 220 are connected by different wires 1212a and 1212b, with the rotating member 121 therebetween. The transmission wire 1212 may enable first-direction driving with a pair of the first power transmission wire 1212a and the second power transmission wire 1212b, or may enable both first-direction driving and second-direction driving with two pairs of the first power transmission wire 1212a and the second power transmission wire 1212b.

The two-step pulley member 1211 may have a donut shape, and an outer surface on which the first pulley part 1211a and the second pulley part 1211b are formed or provided in a groove shape, such that the first power transmission wire 1212a and the second power transmission wire 1212b are seated in and enclosed by the first pulley part 1211a and the second pulley part 1211b. The two-step pulley member 1211 is inserted through a hole formed in a center portion thereof into the transmitting member 122, and is positioned and fixed in an end part of the transmitting member 122, more specifically, a lower part of the transmitting member 122. The two-step pulley member 1211 is coupled to rotate along with rotation of the transmitting member 122. More specifically, the two-step pulley member 1211 may include the first two-step pulley part 1211a and the second two-step pulley part 1211b. The first two-step pulley part 1211a is a part around which the first power transmission wire 1212a is wound, and the second two-step pulley part 1211b is a part that is provided adjacent to the first two-step pulley part 1211a on or under the first two-step pulley part 1211a and around which the second power transmission wire 1212b is wound.

Once the knob part 110 is rotated to generate a triggering force, the rotating member 121, more specifically, the two-step pulley member 1211, is rotated through the transmitting member 122. As the two-step pulley member 1211 rotates, the transmission wires 1212 wound around the groove of the two-step pulley member 1211 are pulled along a rotation direction to generate a tensile force, such that driving is applied to the power generating part 500 and the bending part 220 is manipulated in the left or right direction and/or in the upward or downward direction.

The transmitting member 122 has the main shaft 112 inserted thereinto and rotates along with rotation of the knob part 110 to transmit a triggering force applied to the knob part 110 to the rotating member 121. A pulley coupling part 1221 is provided in a lower part of the transmitting member 122. The pulley coupling part 1221 fixedly supports the two-step pulley member 1211. That is, once the two-step pulley member 1211 is inserted into the pulley coupling part 1221, the pulley coupling part 1221 fixes and supports the two-step pulley member 1211 to couple the two-step pulley member 1211 in such a way to rotate along with rotation of the transmitting member 122. On an upper part of the transmitting member 122, a sensor coupling part 1222 is provided to protrude from an outer surface of the transmitting member 122 and to fix and support the sensor member 123. On an upper part of the sensor coupling part 1222 (hereinafter, referred to as an 'upper transmitting part 1223a'), slot grooves may be formed or provided longitudinally along a rotation axis. A pivot module 1236 (e.g., pivot) of the sensor member 123 of the transmitting member 122 is inserted and fixed into the slot grooves, such that during rotation of the transmitting member 122, the pivot module 1236 is fixed to the upper transmitting part 1223a without rotating.

The sensor member 123 detects an actuating signal according to a triggering force applied to the knob part 110. The sensor member 123 may include a support plate 1231 and a sensor part.

The support plate 1231 is seated and fixed on an upper part of the transmitting member 122, more specifically, the sensor coupling part 1222. The support plate 1231 may include a through-hole 1232 for insertion and fixation in the transmitting member 122 and support protrusions 1233 provided to face each other with respect to the through-hole 1232. The sensor part is mounted on the support plate 1231. The sensor part may include the pivot module 1236, a sensor contact module 1234 (e.g., sensor contact), and sensor modules 1235 (e.g., sensors). The pivot module 1236 is inserted (e.g., provided) into the other-end terminal of the transmitting member 122 (a top end of the transmitting member 122 in the present disclosure). The pivot module 1236 includes an arm part 1236a (e.g., arm) extending in a direction from an outer surface of the pivot module 1236. The arm part 1236a of the pivot module 1236 allows the sensor contact module 1234 to be inserted thereinto. The sensor contact module 1234 is inserted into the arm part 1236a and includes contact parts 1234a (e.g., contacts) at both sides with respect to the arm part 1236a. The sensor contact module 1234 is positioned between the support protrusions 1233, such that the sensor modules 1235 mounted on facing surfaces of the support protrusions 1233 contact the contact parts 1234a at the both sides. The sensor modules 1235 are mounted on the facing surfaces of the support protrusions 1233, such that the sensor contact module 1234 senses a contact and a force corresponding thereto. The sensor module 1235 according to an exemplary embodiment may include a force sensor. Although the sensor part according to the present exemplary embodiment is described as including the foregoing elements, it is understood that one or more other exemplary embodiments are not limited thereto. That is, the sensor part may have any structure or shape as long as it is capable of sensing rotation of the knob part 110.

Figure 5A:
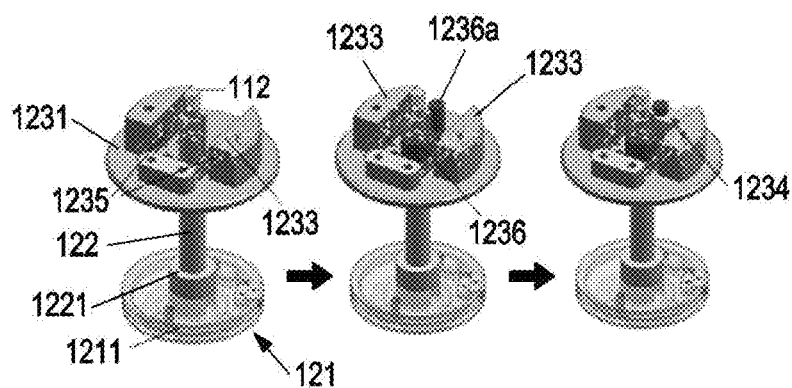
FIGS. 5A to 5C illustrate a coupled state of a knob driving part and a driving state of the knob driving part according to an exemplary embodiment.
Figure 5B:
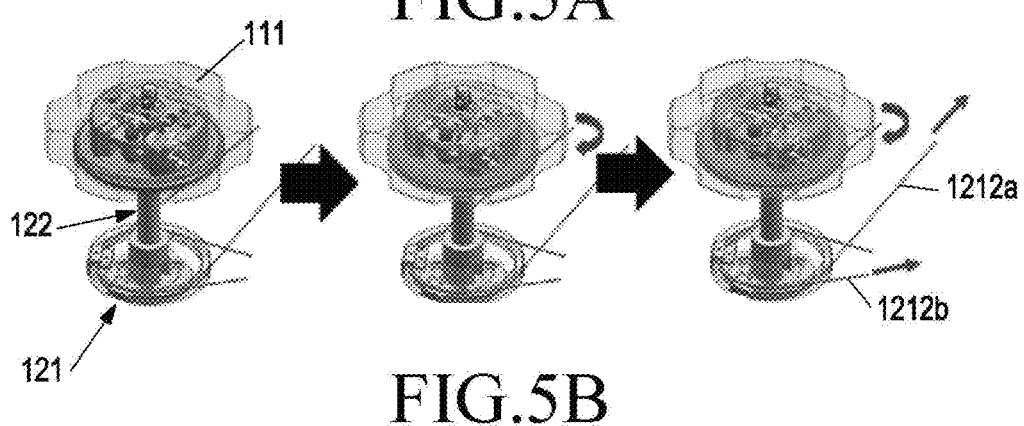
Figure 5C:
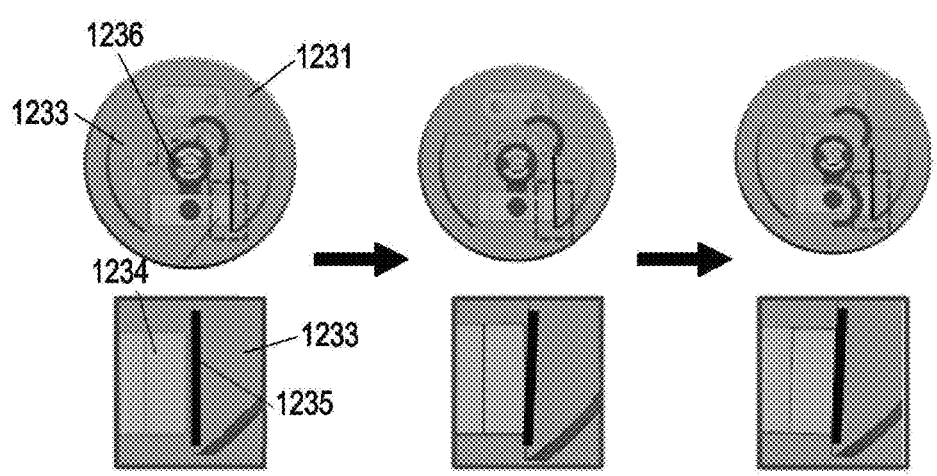

FIGS. 5A to 5C illustrate a coupled state of the knob driving part 100 and a driving state of the knob driving part 100 according to an exemplary embodiment. Referring to FIGS. 5A to 5C, the operation of the knob driving part 100 including the foregoing elements will be described. The transmitting member 122 is inserted into the main shaft 112 of the knob part 110, the rotating member 121 is mounted on a lower part of the transmitting member 122, and the sensor member 123 is mounted on an upper part of the transmitting member 122. Once the support plate 1231 is inserted into the transmitting member 122, the upper transmitting part 1223a protrudes through the through-hole 1232 of the support plate 1231. The pivot module 1236 is mounted on the protruding upper transmitting part 1223a. The arm part 1236a of the pivot module 1236 is positioned between the facing support protrusions 1233, and the sensor contact module 1234 is mounted on the arm part 1236a (see FIG. 5A). In the knob driving part 100 having such a coupled state, once the operator applies a triggering force to the knob part 110, the rotating member 121 rotates in a direction that the triggering force is applied. If the two-step pulley member 1211 rotates in the direction of the triggering force, the first power transmission wire 1212a and the second power transmission wire 1212b wound around the two-step pulley member 1211 are pulled in the direction of the triggering force, thus generating a tensile force. The first power transmission wire 1212a wound between the first two-step pulley part 1211a and the power generating part 500 generates a tensile force as illustrated by arrow in FIG. 5B, and the second power transmission wire 1212b wound between the second two-step pulley part 1211b and the bending part 220 also generates a tensile force as illustrated by arrow in FIG. 5B.

Referring to FIG. 5C, the operation of the sensor module 1235 corresponding to the triggering force applied to the knob part 110 will now be Prior to driving of the knob part 110, the sensor contact module 1234 is provided between the support protrusions 1233, such that the sensor contact module 1234 and the sensor module 1235 are maintained to be spaced apart from each other by a predetermined interval. If the triggering force is applied to the knob part 110 in this the support plate 1231 rotates while the pivot module 1236 is fixed. Along with rotation of the support plate 1231, the support protrusion 1233 at a side and the sensor module 1235 at a side contact each other. Thus, a contact signal is applied to the system, and driving of the power generating part 500 to be described below is controlled by a detection signal applied to the system.

The endoscope device 10 according to one or more exemplary embodiments may include one or more gap reducing devices 600, 400, and 700. In an exemplary embodiment, the endoscope device 10 will be described as including three gap reducing devices, although it is understood that one or more other exemplary embodiments are not limited thereto. The first gap reducing device 600 compensates for a gap of the transmission wire 1212 provided on the first member 11, the second gap reducing device 400 compensates for a gap of the transmission wire 1212 provided on the second member 12, and the third gap reducing device 700 compensates for a gap generated in the power generating part 500 (see FIGS. 1, 2A, 2B, and 19).

Herein, the first gap reducing device 600 will now be described with reference to FIGS. 6A to 6C.

FIGS. 6A to 6C illustrate the first gap reducing device 600 in the endoscope device 10 according to an exemplary embodiment, and FIGS. 7A and 7B are enlarged views of FIG. 6B.

Referring to FIGS. 6A to 6C and 7A to 7B, as stated above, the first gap reducing device 600 reduces a gap of the transmission wire 1212 provided on the first member 11 (see FIG. 1). The first gap reducing device 600 is provided inside a body of the knob part 110 between the knob driving part 100 and an insertion tube 210 (see FIGS. 2A and 2B). The first gap reducing device 600 may include a gap housing 610, a wire contact part 620 (e.g., wire contact), and a rotation angle adjusting part 630 (e.g., rotation angle adjuster). The gap housing 610 is fixed inside a knob body 13 to allow rotation of the wire contact part 620. The wire contact part 620 is mounted on the gap housing 610 in such a way to be rotatable. The wire contact part 620 may have a structure of a cantilever having a degree of freedom in rotation. An end 621 of the wire contact part 620 is coupled to the inside of the body of the knob part 110 to rotate around a rotation axis, and another end 622 of the wire contact part 620 applies a force to the transmission wire 1212, more specifically, the second power transmission wire 1212b, to compensate for a gap generated in the second power transmission wire 1212b. The rotation angle adjusting part 630 adjusts a rotation angle of the wire contact part 620, and supports the wire contact part 620 to fix the wire contact part 620 at a predetermined angle. The rotation angle adjusting part 630 may include an adjustment screw passing through a knob body 13 from the outside of the knob body 13, and the rotation angle adjusting part 630 adjusts an angle of the wire contact part 620 by applying a force to the other surface of the wire contact part 620.

Thus, referring to FIG. 2A, with the rotation angle adjusting part 630, another end 622 of the wire contact part 620 provides a force (a compressive force) to the second power transmission wire 1212b to reduce a gap of the second power transmission wire 1212b generated between the bending part 220 and the knob driving part 100.

Figure 8:
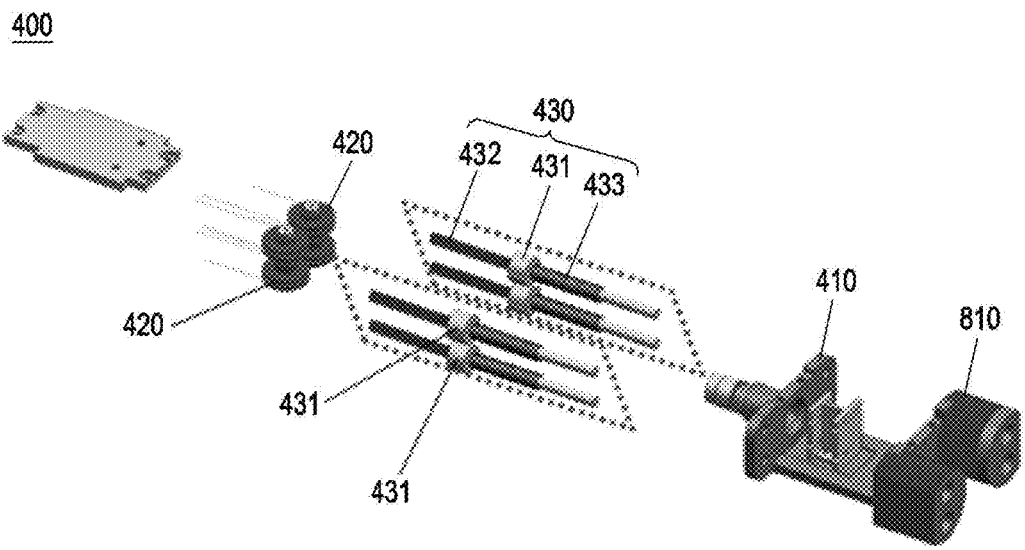
FIG. 8 illustrates an exploded state of a power transmitting part in an endoscope device according to an exemplary embodiment.
Figures 9A, 9B, 9C:
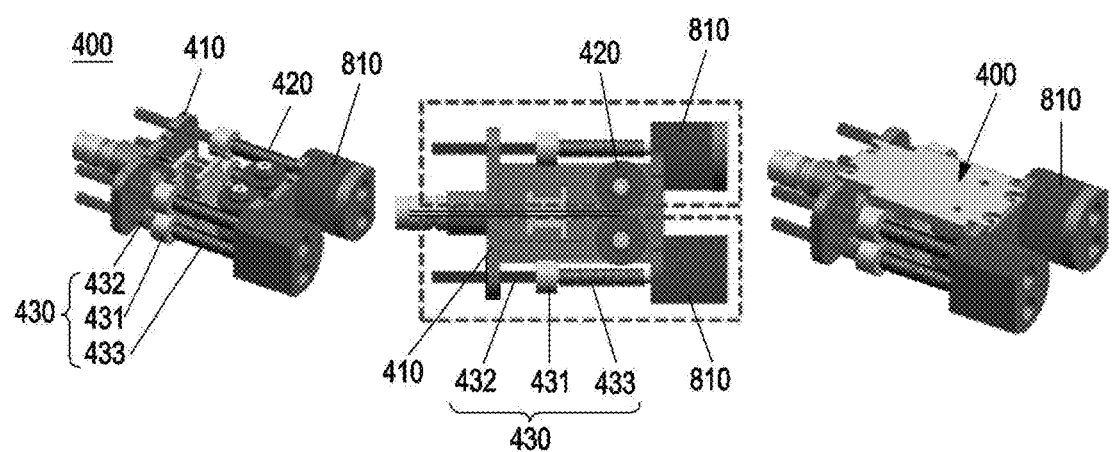
FIGS. 9A to 9C illustrate a coupled state of a power transmitting part in an endoscope device according to an exemplary embodiment.
Figure 10:
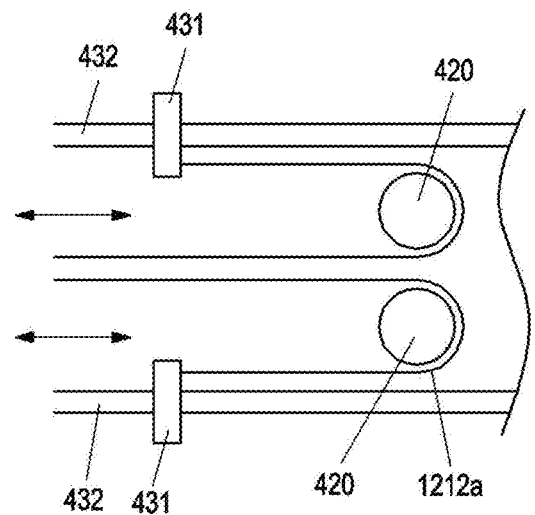
FIG. 10 schematically illustrates FIG. 9B.

FIG. 8 illustrates an exploded (i.e., decoupled) state or view of the power transmitting part 400 in the endoscope device 10 according to an exemplary embodiment. FIGS. 9A to 9C illustrate a coupled state of the power transmitting part 400 in the endoscope device 10 according to an exemplary embodiment. FIG. 10 schematically illustrates FIG. 9B.

Referring to FIGS. 8, 9A to 9C, and 10, the power transmitting part 400 is provided between the knob driving part 100 and the power generating part 500 (see FIGS. 1, 2A, and 2B). The power transmitting part 400 (hereinafter, referred to as 'the second gap reducing device 400') may include a frame 410, a direction change pulley part 420 (e.g., direction change pulley), a displacement adjusting part 430 (e.g., displacement adjuster), and a displacement-adjusting elastic part 433. The frame 410 is provided between the knob driving part 100 and the power generating part 500, such that the displacement adjusting part 430 and the displacement-adjusting elastic part 433 are mounted inside the frame 410. The direction change pulley part 420 may be provided in pairs to enclose the first-direction transmission wire 1212 and the second-direction transmission wire 1212. More specifically, one direction-change pulley part (e.g., first direction-change pulley) may have a dumbbell shape and encloses the first power transmission wire 1212a with protruding parts at both sides thereof. The displacement adjusting part 720 is coupled to the frame 410 in such a way to move and the first power transmission wire 1212a is fixed, thereby providing translational motion of the first power transmission wire 1212a. The displacement adjusting part 430 adjusts a gap of the first power transmission wire 1212a according to driving of the power generating part 500. The displacement adjusting part 430 includes a guide part 431 and an adjusting guide 432. The guide part 431 is coupled to the frame 410 in such a way to move, and the adjusting guide 432 extends from the guide part 431 and fixes an end part of the first power transmission wire 1212a. Thus, driving of the power generating part 500 is provided to the displacement adjusting part 430 which then moves in a direction. As the displacement adjusting part 430 moves, the first power transmission wire 1212a fixed on the adjusting guide 432 is pulled and thus generates a tensile force, thereby compensating for a gap.

To couple the second gap reducing device 400 with the power generating part 500, a coupling device 800 is also provided (see FIG. 11). The coupling device 800 may include a first coupling part 810 provided on the second gap reducing device 400 and a second coupling part 820 provided on the power generating part 500. The first coupling part 810 protrudes from the second gap reducing device 400, more specifically, an end of the frame 410, and is seated in the second coupling part 820. A detailed operation or structure thereof will be described below.

Figure 12:
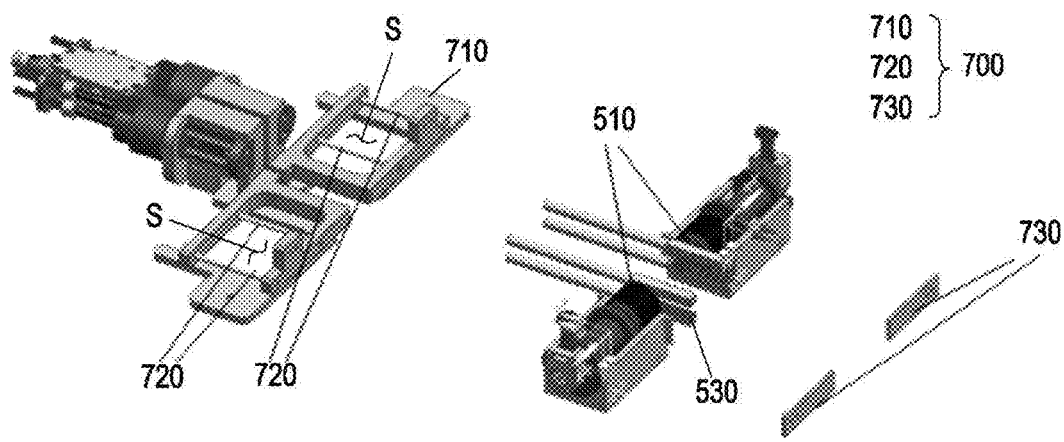
FIG. 12 illustrates a coupled state of some elements of a power transmitting part according to an exemplary embodiment.

FIG. 11 illustrates the power generating part 500 according to an exemplary embodiment, and FIG. 12 illustrates a coupled state of some elements of the power generating part 500 according to an exemplary embodiment. FIGS. 13A, 13B, 14A, and 14B illustrate a coupled state of the power generating part 500 according to an exemplary embodiment, and FIG. 15 is an enlarged view illustrating a coupled state of the power generating part 500 according to an exemplary embodiment.

Referring to FIGS. 11 through 15, the power generating part 500 may include one or more driving members 510 (e.g., drivers), a torque sensor member 520 (e.g., torque sensor), and a gear member 530 (e.g., gear).

The driving member 510 provides a driving force like a motor, and is provided in pairs at both sides for driving control in the first direction and in the second direction. The torque sensor member 520 is connected to the driving member 510 and senses torque generated in the driving member 510 during driving of the driving member 510. That is, a system load applied to the driving member 510 like a motor is measured in the torque sensor member 520 to detect and monitor a change in the system load on a real time basis. The gear member 530 is provided in an end of the driving member 510 to transmit a driving force of the driving member 510 to the second gap reducing device 400 (the power transmission part 400). The gear member 530 may include a pinion gear 531 and a rack gear 532. The pinion gear 531 is connected to the driving member 510 and is engaged to the rack gear 532 to transmit rotation of the driving member 510 to the rack gear 532. The rack gear 532 is provided in pairs on a top surface and a bottom surface of the pinion gear 531 such that the pair of rack gears 532 are engaged with each other, thus transforming a driving force corresponding to rotation into a forward driving force. As the pinion gear 531 rotates, the rack gears 532 move in opposite directions to each other.

The pair of rack gears 532 of the power generating part 500 contact the displacement adjusting part 430 of the power transmitting part 400 to transmit power. The pair of rack gears 532 move in opposite directions, such that a rack gear 532b (a lower rack gear 532b in FIG. 15) providing a compressive force and the displacement adjusting part 430 contacting the rack gear 532b (referred to as a 'second displacement adjusting part 430b') are driven in the same direction, and at the same time, the displacement adjusting part 430 (referred to as a 'first displacement adjusting part 430a') contacting an upper rack gear 532a is stretched in contact with the upper rack gear 532a by a tensile force of the first power transmission wire 1212a. In this way, as the rotating direction of the driving member 510 changes, the moving direction of the rack gear 532 and the displacement adjusting part 430 changes (see FIGS. 20A and 20B).

The power generating part 500 may further include the third gap reducing device 700 (hereinafter, referred to as the 'gap absorbing device 700' or a 'gap absorbing member') that controls a gap of the power generating part 500, generated by driving of a driving motor.

The gap absorbing device 700 may include a housing 710, a gap guide part 720 (e.g., gap guide), and a gap elastic part 730. The housing 710 may include a seating part S (e.g., seat) on which the power generating part 500 is seated. The gap guide part 720 is provided on the seating part S and provides a degree of freedom of translational motion along the rack gear 532 of the power generating part 500. The gap elastic part 730 provides elasticity to the power generating part 500 that makes a translational motion on the gap guide part 720 toward an end part of the seating part S.

Figure 16A:
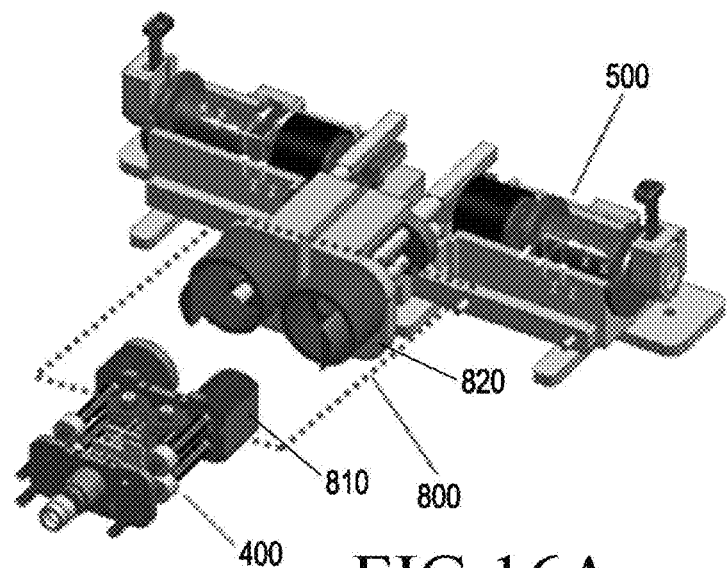
FIGS. 16A to 16C illustrate a state where a power transmitting part and a power generating part are not coupled according to an exemplary embodiment.
Figure 16B:
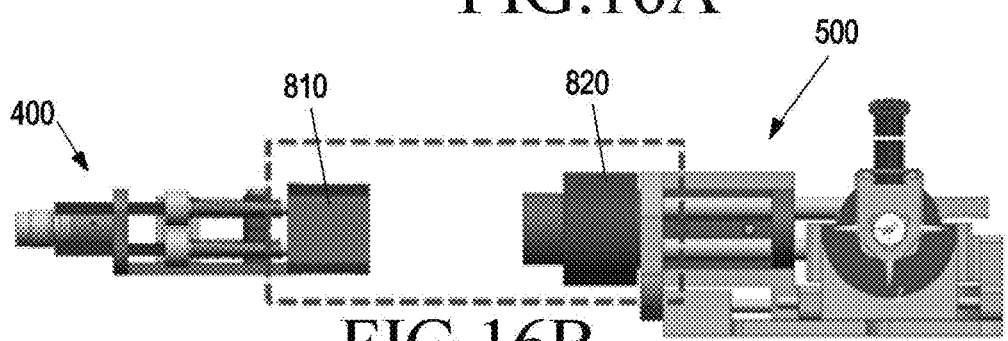
Figure 16C:
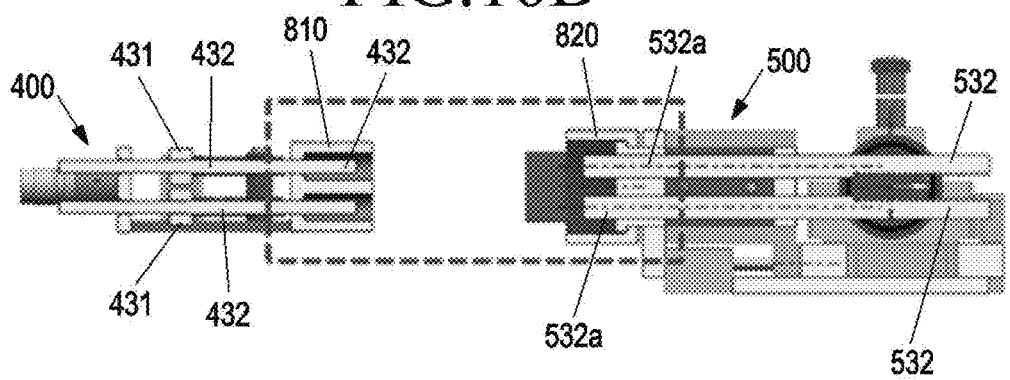
Figure 17:
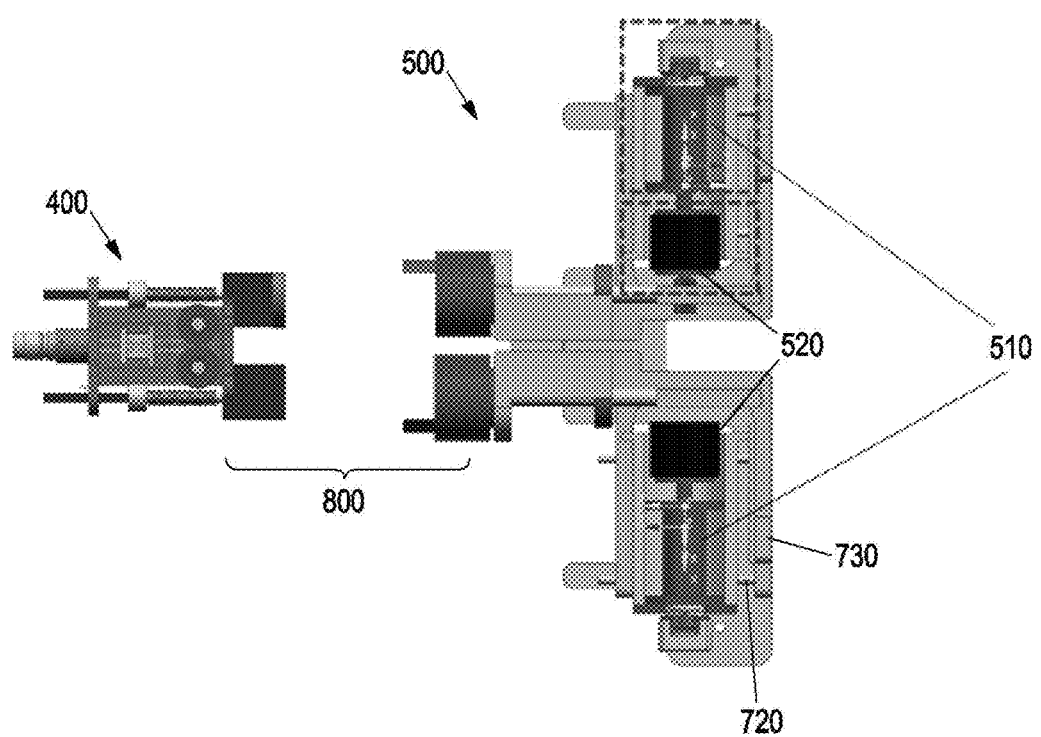
FIG. 17 illustrates a state of FIG. 16 viewed in another direction.
Figure 18A:
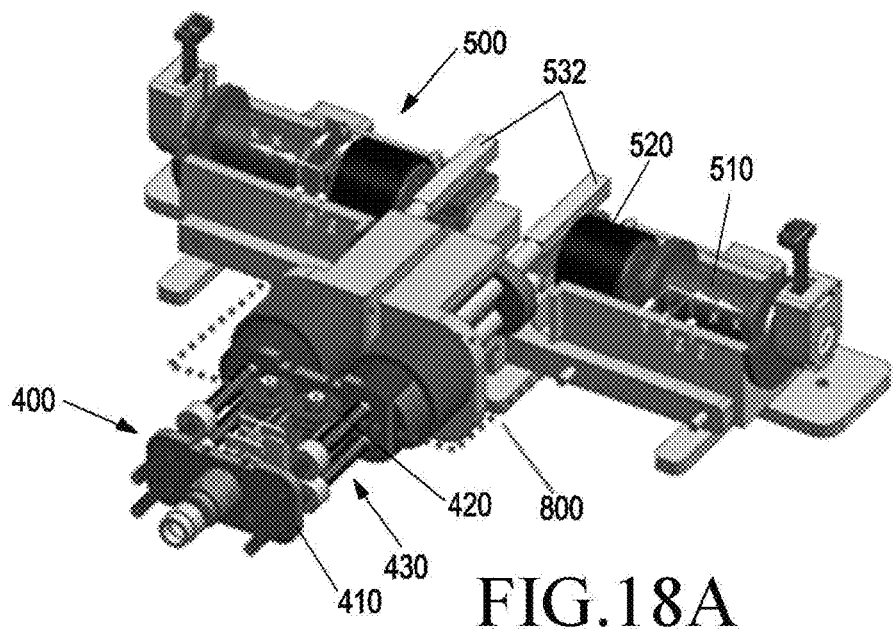
FIGS. 18A to 18C illustrate a state where a power transmitting part and a power generating part have been coupled according to an exemplary embodiment.
Figure 18B:
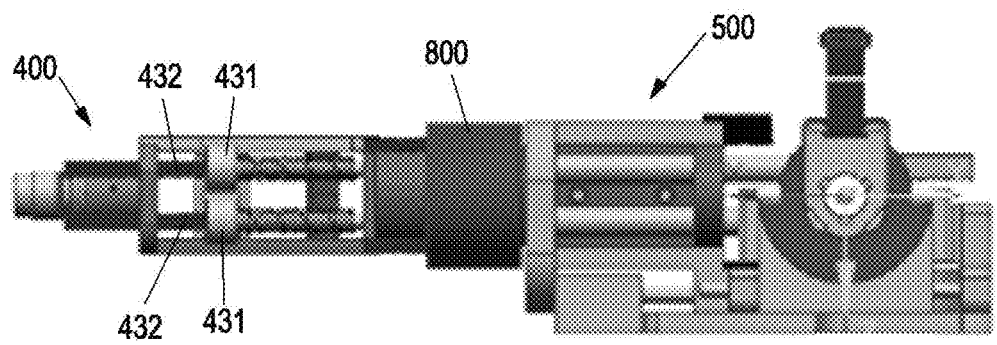
Figure 18C:
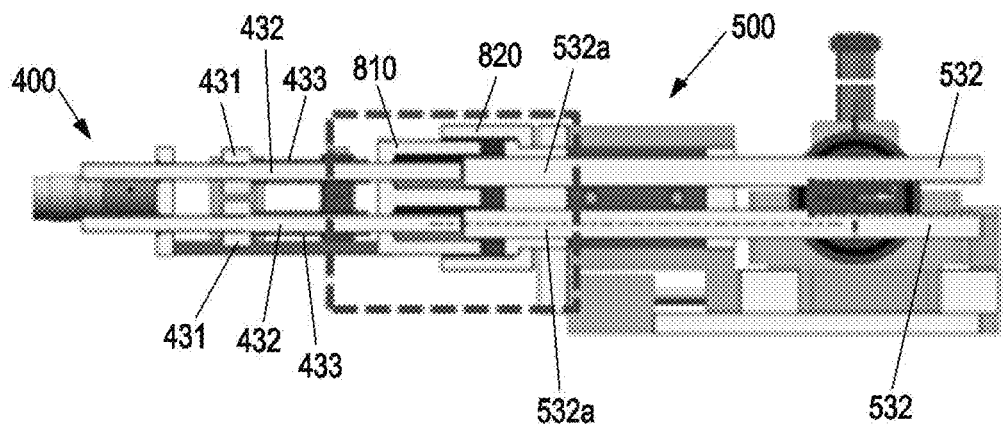
Figure 19:
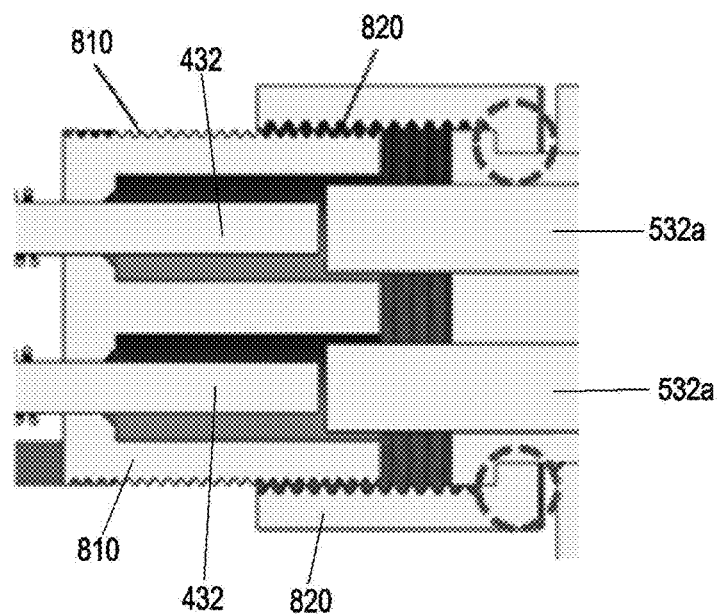
FIGS. 19 and 20A and 20B illustrate a coupled state of a coupling device and a driving state of the coupling device according to an exemplary embodiment.
Figure 20A:
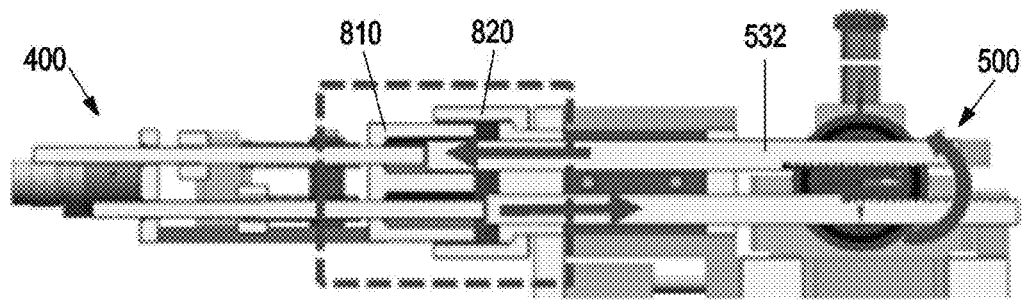
Figure 20B:
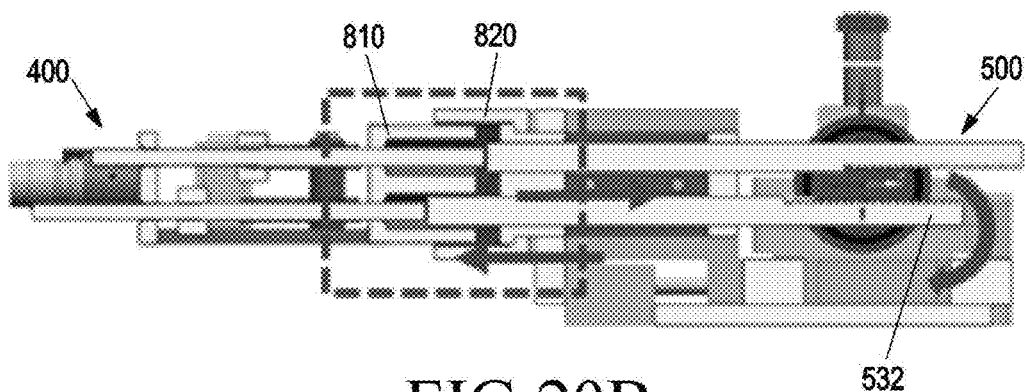

FIGS. 16A to 16C illustrate a state in which the power transmitting part 400 and the power generating part 500 are not coupled according to an exemplary embodiment, and FIG. 17 illustrates FIGS. 16A to 16C viewed from a different direction. FIGS. 18A to 18C illustrate a state in which the power transmitting part 400 and the power generating part 500 have been coupled according to an exemplary embodiment, and FIGS. 19 and 20A to 20B illustrate a coupled state and a driving state of the coupling device 800 according to an exemplary embodiment.

Referring to FIGS. 16A to 16C, 17, 18A to 18C, 19, and 20A to 20B, the coupling device 800 for coupling the power transmitting part 400 with the power generating part 500 is illustrated. As described above, the coupling device 800 may include a first coupling part 810 and a second coupling part 820. The first coupling part 810 is provided on the power transmitting part 400, more specifically, at a side of the frame 410, and in the present exemplary embodiment, the first coupling part 810 includes a male screw part that forms a screw thread on an outer side thereof. The second coupling part 820 protrudes from the power generating part 500, more specifically, a side of the housing 810, such that the first coupling part 810 is seated on and coupled to the second coupling part 820. In the present exemplary embodiment, the second coupling part 820 includes a female screw part forming a screw thread on an inner side thereof. Thus, a distance between the power transmitting part 400 and the power generating part 500 may be adjusted according to a distance that the first coupling part 810 and the second coupling part 820 are engaged, more specifically, a distance the male screw part is inserted into the female screw part by means of rotation.

The second coupling part 820 includes a protruding part 532a (e.g., protrusion) extending from the rack gear 532 and the first coupling part 810 includes the adjusting guide 432, such that once the first coupling part 810 and the second coupling part 820 are engaged with each other, the adjusting guide 432 and an end part of the protruding part 532a that are provided on the same plane are connected in close contact with each other. Thus, movement of the protruding part 532a is provided to the adjusting guide 432.

That is, the female screw part that binds the power generating part 500 in the direction of translation and the male screw part of the power transmitting part 400 are coupled to each other, thereby reducing the distance between the power generating part 500 and the power transmitting part 400. As the distance between the power generating part 500 and the power transmitting part 400 decreases, the pair of rack gears 532 of the power generating part 500 contact the adjusting guide 432 of the power transmitting part 400 and a compressive force is applied to the adjusting guide 432, thereby reducing a gap.

Figure 21:
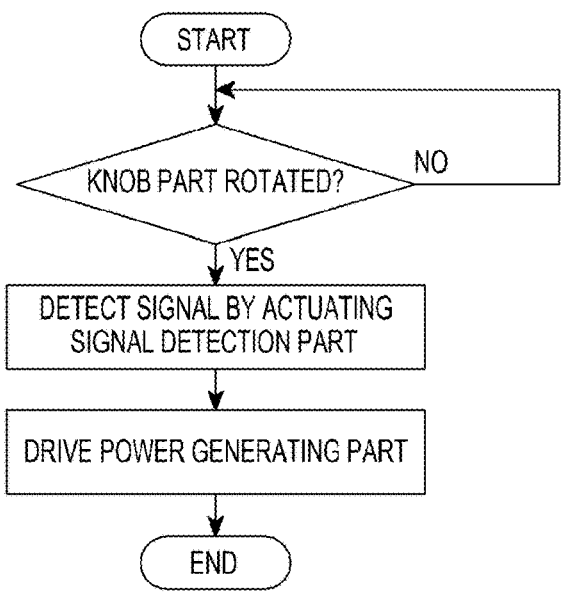
FIGS. 21 and 22 are flowcharts illustrating operations of an endoscope device according to an exemplary embodiment.
Figure 22:
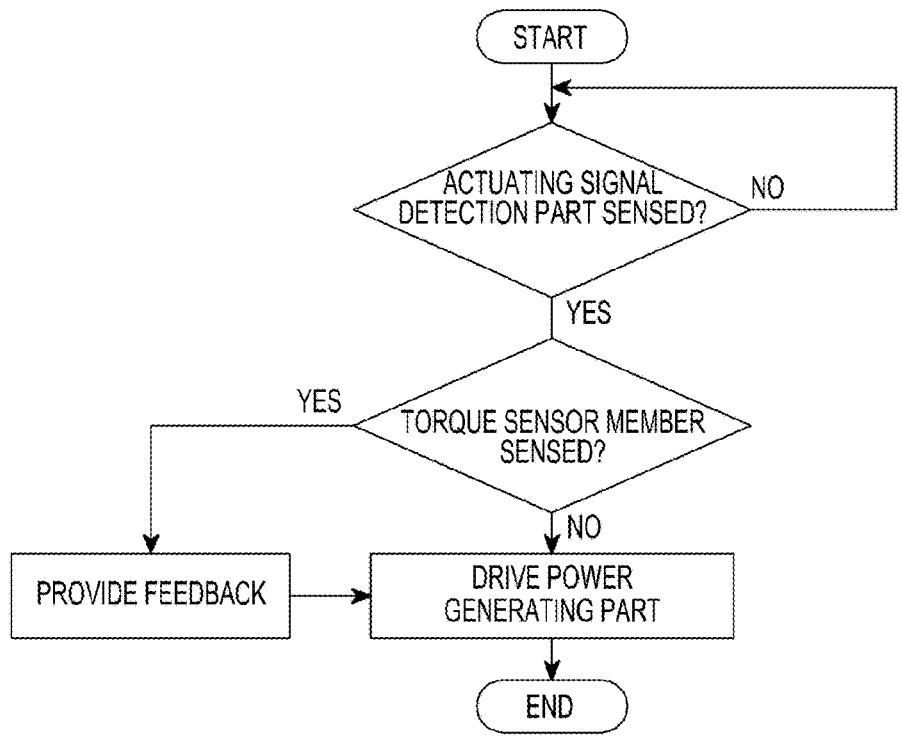

FIGS. 21 and 22 are flowcharts schematically illustrating the automatic manipulation mode, the manual manipulation mode, and feedback control of the endoscope device 10 according to one or more exemplary embodiments, and a detailed description of FIGS. 21 and 22 will comply with the foregoing description.

The endoscope device 10 according to one or more exemplary embodiments may be manipulated by the operator with a smaller force than in a related art endoscope device, may lower the operator's degree of fatigue, and may allow the operator to easily control manipulation.

The endoscope device 10 according to one or more exemplary embodiments may implement an automatic driving mode and a manual driving mode, and in a normal situation, the endoscope device may be used in the automatic mode, and upon occurrence of an emergency situation during the examination of a subject (examinee) by the operator, the automatic mode may be switched to the manual mode.

The endoscope device 10 according to one or more exemplary embodiments may improve response characteristics when being used in the automatic mode.

The endoscope device 10 according to one or more exemplary embodiments may sense a triggering force generated in the front end part of the distal end and provide feedback to the operator.

The endoscope device 10 according to one or more exemplary embodiments may improve position control precision and minimize a gap generated during direction change when the operator is examined.

The endoscope device 10 according to one or more exemplary embodiments may accurately detect a triggering force corresponding to a driving actuating signal applied to a knob driving part.

The endoscope device 10 according to one or more exemplary embodiments may facilitate detachment/attachment and coupling of modules provided therein to make sterilization easy and to facilitate replacement of damaged or broken modules, and may reduce a gap that may be generated during coupling of the modules or driving of the endoscope device.

Furthermore, the endoscope device 10 according to one or more exemplary embodiments may perform position holding without applying separate locking to the knob driving part.

In addition, the endoscope device 10 according to one or more exemplary embodiments may provide to an operator, feedback, such as haptic feedback, with respect to a factor measured as disturbance after detecting driving torque of the knob driving part.

Other effects that may be obtained or expected from practice of exemplary embodiments are explicitly or implicitly disclosed in the detailed description of exemplary embodiment. For example, various effects expected from exemplary embodiments have been disclosed in or may be understood from the detailed description of exemplary embodiments.

While exemplary embodiments have been particularly shown and described above, various changes in form and detail may be made therein without departing from the spirit and scope of the present inventive concept as defined by the following claims. Accordingly, the scope of the present inventive concept will be defined by the appended claims and equivalents thereto.

What is claimed is:

1. An endoscope device including a knob driver comprising:
    a knob driver configured to be driven in a mode selected by an operator from either of an automatic mode and a manual mode;
    a bending member connected to the knob driver and configured to change a position of a distal end of the endoscope device by driving of the knob driver;
    a power generator configured to provide power to the knob driver; and
    a power transmitter configured to drive the power generator according to a manipulation of the knob driver,
    wherein in the automatic mode, a triggering force applied to the knob driver by an operator of the endoscope device is detected by the knob driver, and the power generator is driven to provide a driving force for the knob driver according to the detected triggering force to change the position of the distal end, and
    wherein in the manual mode, the detected triggering force applied to the knob driver is provided to the bending member to change the position of the distal end.

2. The endoscope device including the knob driver of claim 1, wherein the knob driver comprises:
    a knob part configured to receive a triggering force from an operator; and
    an actuating signal detector configured to detect the received triggering force.

3. The endoscope device including the knob driver claim 2, wherein the actuating signal detector comprises:
    a rotating member in the knob part and configured to transmit a rotation of the knob part to the power generator and the bending member;
    a transmitting member on a main shaft of the knob part and configured to transmit the received triggering force applied to the knob part to the rotating member; and
    a sensor member configured to detect an actuating signal according to the received triggering force.

4. The endoscope device including the knob driver of claim 3, wherein the rotating member comprises:

a two-step pulley member in an end part of the transmitting member;
a first transmitting wire extending between the two-step pulley member and the power generator and configured to transmit rotational driving of the two-step pulley member; and
a second transmitting wire extending between the two-step pulley member and the bending member and configured to transmit rotational driving of the two-step pulley member.

5. The endoscope device including the knob driver of claim 4, wherein the two-step pulley member comprises:
a first two-step pulley part around which the first power transmission wire is wound; and
a second two-step pulley part on an upper side or a lower side of the first two-step pulley part and around which the second power transmission wire is wound.

6. The endoscope device including the knob driver of claim 5, further comprising a first gap reducing member in the knob driver, the first gap reducing member configured to compensate for a gap of the second power transmission wire between the bending member and the knob driver.

7. The endoscope device including the knob driver of claim 6, wherein the first gap reducing member comprises:
a gap housing provided inside a body of the knob part;
a wire contact part rotatably mounted in the gap housing and configured to rotate around a rotation axis to apply a force to the second power transmission wire; and
a rotation angle adjusting member configured to adjust a rotation angle of the wire contact part.

8. The endoscope device including the knob driver of claim 3, wherein the actuating signal detector further comprises:
a pulley coupling part in a lower part of the transmitting member, the pulley coupling part configured to rotatably couple the two-step pulley member; and
a sensor coupling part in an upper part of the transmitting member, the sensor coupling part configured to fixedly support the sensor member.

9. The endoscope device including the knob driver of claim 5, wherein the sensor member comprises:
a support plate in an upper part of the transmitting member; and
a sensor part on the support plate, the sensor part configured to sense rotation of the knob part.

10. The endoscope device including the knob driver of claim 9, wherein the support plate comprises:
a through-hole inserted and fixed in the transmitting member; and
support protrusions provided to face each other on opposing sides of the through-hole.

11. The endoscope device including the knob driver of claim 10, wherein the sensor part comprises:
a pivot inserted into an another-end terminal of the transmitting member and comprising an extending arm part;
a sensor contact member inserted into the arm part and positioned between the support protrusions; and
a sensor on facing surfaces of the support protrusions configured to sense a contact by the sensor contact member.

12. The endoscope device of claim 10, wherein the power generating part comprises:
one or more driving members configured to provide a driving force;
a torque sensor member connected to the one or more driving members; and
a gear member connected to the one or more driving members.

13. The endoscope device of claim 12, wherein the gear member comprises:
a pinion gear connected to the one or more driving members; and
rack gears respectively engaged on a top surface and a bottom surface of the pinion gear.

14. The endoscope device of claim 13, wherein the power generating part further comprises a gap absorbing member configured to control a gap of the power generating part, generated by driving of the one or more driving members.

15. The endoscope device of claim 14, wherein the gap absorbing member comprises:
a housing comprising a seating part on which the power generating part is seated;
a gap guide part on the seating part and configured to provide a degree of freedom of translational motion along the rack gears of the power generating part; and
a gap elastic part configured to provide elasticity to the power generating part that allows a translational motion to an end part of the seating part on the gap guide part.

16. The endoscope device of claim 13, wherein the power transmitting part comprises:
a frame between the knob driving part and the power generating part;
a direction change pulley part on the frame and configured to change a direction of the first power transmission wire;
a displacement adjusting part movably coupled to the frame and configured to fix the first power transmission wire and to provide a translational motion; and
a displacement adjusting elastic part on the displacement adjusting part and configured to provide an elastic force to the displacement adjusting part.

17. The endoscope device of claim 16, wherein the displacement adjusting part comprises:
a guide part movably coupled to the frame; and
an adjusting guide part coupled to the guide part and configured to fix an end part of the first power transmission wire and to control a degree of freedom in the translational motion of the first power transmission wire.

18. The endoscope device of claim 16, further comprising a coupling device is between the power transmitting part and the power generating part.

19. The endoscope device of claim 18, wherein the coupling device comprises:
a first coupling part on the power transmitting part; and
a second coupling part engaged with the first coupling part and on the power generating part,
wherein a distance between the power transmitting part and the power generating part is adjusted according to a distance that the first coupling part and the second coupling part are engaged.

20. The endoscope device of claim 19, further comprising:
protruding parts extending from the rack gears to the second coupling part,
wherein the adjusting guide extends to the first coupling part, such that if the first coupling part and the second coupling part are engaged and coupled to each other, the guide part and the protruding parts contact such that driving of the protruding parts is transmitted to the guide part.

21. The endoscope device including the knob driver of claim 2, wherein in the automatic mode, a signal corresponding to the received triggering force applied to the knob part is detected by the actuating signal detector and the power generator is driven, via the power transmitter, according to the detected signal.

22. The endoscope device including the knob driver of claim 2, wherein in the manual mode, the received triggering force applied to the knob part is provided to the bending member and the power generator at a same time, to change the position of the distal end.

23. The endoscope device including the knob driver of claim 2, wherein in the automatic mode:
the received triggering force is detected by the actuating signal detector;
a driving force is provided by the power generator according to the detected triggering force;
the driving force of the power generator is transmitted to a two-step pulley member of the knob driver through the power transmitter; and
the driving force transmitted to the two-step pulley member is transmitted to the bending member to change the position of the distal end.

24. The endoscope device including the knob driver of claim 23, wherein:
the power generator comprises a torque sensor member; and
in the automatic mode, the torque sensor member is configured to sense a disturbance and to adjust a rotation speed of the knob part based on a comparison between the sensed disturbance and the detected triggering force.

25. An endoscope device including a knob driver comprising:
a knob driver configured to be driven in a mode selected by an operator from either of an automatic mode or a manual mode;
a bending member connected to the knob driver and configured to change a position of a distal end of the endoscope device by driving of the knob driver; and
a power generator configured to provide power to the knob driver according to a manipulation of the knob driver,
wherein in the automatic mode, a triggering force applied to the knob driver by an operator of the endoscope device is detected by the knob driver, and the power generator is driven to provide a driving force for the knob driver according to the detected triggering force to change the position of the distal end, and
wherein in the manual mode, the detected triggering force applied to the knob driver is provided to the bending member to change the position of the distal end.

26. The endoscope device including the knob driver of claim 25, wherein:
in the automatic mode, the driving force of the power generator is transmitted to a two-step pulley member extending between the knob driver and the power generator; and
the driving force transmitted to the two-step pulley member is transmitted to the bending member to change the position of the distal end.

27. The endoscope device including the knob driver of claim 23, wherein:
the power generator comprises a torque sensor member; and
in the automatic mode, the torque sensor member is configured to sense a disturbance and to adjust a rotation speed of the knob driver based on a comparison between the sensed disturbance and the detected triggering force.

28. A method of operating an endoscope device, the method comprising:
detecting a triggering force applied by an operator of the endoscope device to a knob driving part of the endoscope device configured to be driven in a mode selected by an operator from either of an automatic mode and a manual mode;
driving, in the automatic mode, a power generating part of the endoscope device according to the detected triggering force, to provide a driving force for the knob driving part according to the detected triggering force so as to change a position of a distal end of the endoscope device; and
providing, in the manual mode, the detected triggering force to a bending part of the endoscope device to change the position of the distal end.

29. The method of claim 28, wherein the driving the power generating part in the automatic mode comprises:
transmitting the driving force of the power generating part to a two-step pulley member extending between the knob driving part and the power generating part; and
transmitting the driving force transmitted to the two-step pulley member to the bending part to change the position of the distal end.

30. The endoscope of claim 28, wherein the driving the power generating part in the automatic mode comprises:
sensing, by a torque sensor member of the power generating part, a disturbance; and
adjusting a rotation speed of the knob driving part based on a comparison between the sensed disturbance and the detected triggering force.

* * * * *